(12) United States Patent
Byun et al.

(10) Patent No.: US 11,964,935 B2
(45) Date of Patent: Apr. 23, 2024

(54) GINGEROL DERIVATIVE HAVING INHIBITORY ACTIVITY AGAINST BIOFILM FORMATION AND PHARMACEUTICAL COMPOSITION COMPRISING SAME AS EFFECTIVE INGREDIENT FOR PREVENTING OR TREATING BIOFILM-CAUSED INFECTION SYMPTOM

(71) Applicants: Korea University Research and Business Foundation, Sejong Campus, Sejong (KR); Korea University Research and Business Foundation, Seoul (KR)

(72) Inventors: Youngjoo Byun, Daejeon (KR); Hee-Deung Park, Seongnam-si (KR); Sang-Hyun Son, Daejeon (KR); Eunji Cha, Seoul (KR); So-Young Ham, Seongnam-si (KR); Hyunsuk Choi, Seongnam-si (KR)

(73) Assignees: Korea University Research and Business Foundation, Sejong Campus, Sejong (KR); Korea University Research and Business Foundation, Seoul (KR)

( * ) Notice: Subject to any disclaimer, the term of this patent is extended or adjusted under 35 U.S.C. 154(b) by 738 days.

(21) Appl. No.: 16/632,592

(22) PCT Filed: Jul. 19, 2018

(86) PCT No.: PCT/KR2018/008171
§ 371 (c)(1),
(2) Date: Apr. 27, 2020

(87) PCT Pub. No.: WO2019/017709
PCT Pub. Date: Jan. 24, 2019

(65) Prior Publication Data
US 2020/0283364 A1 Sep. 10, 2020

(30) Foreign Application Priority Data

Jul. 20, 2017 (KR) .................. 10-2017-0092270
Jul. 6, 2018 (KR) .................. 10-2018-0078859

(51) Int. Cl.
*C07C 49/255* (2006.01)
*A61P 31/04* (2006.01)
*C07C 49/245* (2006.01)

(52) U.S. Cl.
CPC ............ *C07C 49/255* (2013.01); *A61P 31/04* (2018.01); *C07C 49/245* (2013.01)

(58) Field of Classification Search
CPC ...... C07C 49/255; C07C 49/245; A61P 31/04; A61K 31/12; A61K 31/05
See application file for complete search history.

(56) References Cited

FOREIGN PATENT DOCUMENTS

| JP | 2002-47195 A | 2/2002 |
| KR | 10-1254740 B1 | 4/2013 |
| WO | WO 2007/104985 A1 | 9/2007 |

OTHER PUBLICATIONS

Morera Bioorganic & Medicinal Chemistry Letters 22 (2012) 1674-1677.*
Denniff, et al. J. Chem Soc. Perkin I, 1081, p. 82-87.*
Chemical Abstract compound, STN express. See RN 1027089-59-3 (Entered STN: Jun. 10, 2008).
Chemical Abstract compound, STN express. See RN 1349217-33-9 (Entered STN: Dec. 5, 2011).
Chemical Abstract compound, STN express. See RN 1823471-70-0 (Entered STN: Dec. 6, 2015).
Kim, Han-Shin et al., "6-Gingerol reduces Pseudomonas aeruginosa biofilm formation and virulence via quorum sensing inhibition", *Scientific Reports*, vol. 5, 2015 (pp. 1-11).
Kim, Han-Shin et al., "Raffinose, a plant galactoside, inhibits Pseudomonas aeruginosa biofilm formation via binding to LecA and decreasing cellular cyclic diguanylate levels", *Scientific Reports*, vol. 6, 2016, (pp. 1-10).
Choi, Hyunsuk et al., "Structure—Activity Relationships of 6- and 8-Gingerol Analogs as Anti-Biofilm Agents", *J. Med. Chem*, vol. 60, 2017 (pp. 9821-9837).
Kushwaha, Manoj et al., "Establishment of LCMS Based Platform for Discovery of Quorum Sensing Inhibitors: Signal Detection in Pseudomonas aeruginosa PAO1", *ACS Chem. Biol*, 2018 (pp. 1-24).
International Search Report dated Nov. 2, 2018 in counterpart International Patent Application No. PCT/KR2018/008171 (3 pages in English and 3 pages in Korean).

* cited by examiner

*Primary Examiner* — Ana Z Muresan
(74) *Attorney, Agent, or Firm* — NSIP Law

(57) ABSTRACT

The present invention relates to a gingerol derivative having inhibitory activity against biofilm formation and a pharmaceutical composition for preventing or treating infections caused by biofilms including the gingerol derivative as an active ingredient. The gingerol derivative of the present invention exhibits significantly improved binding affinity for LasR and inhibitory activity against biofilm formation. Therefore, the gingerol derivative of the present invention can act on various membrane surfaces where biofilms tend to form and can effectively inhibit the formation of the corresponding biofilms. In addition, the use of the pharmaceutical composition according to the present invention can fundamentally prevent or treat a variety of infections caused by biofilms due to the presence of the gingerol derivative in the pharmaceutical composition.

6 Claims, 8 Drawing Sheets

[Fig. 1]
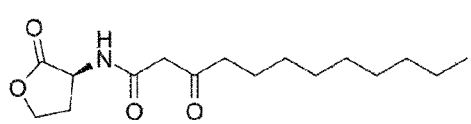
OdDHL (1a)
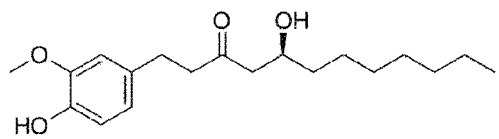
(S)-8-Gingerol (1c)
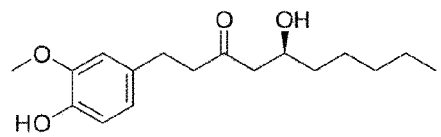
(S)-6-Gingerol (1b)
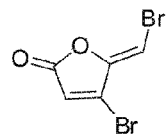
Furanone C-30 (1d)
[Fig. 2]
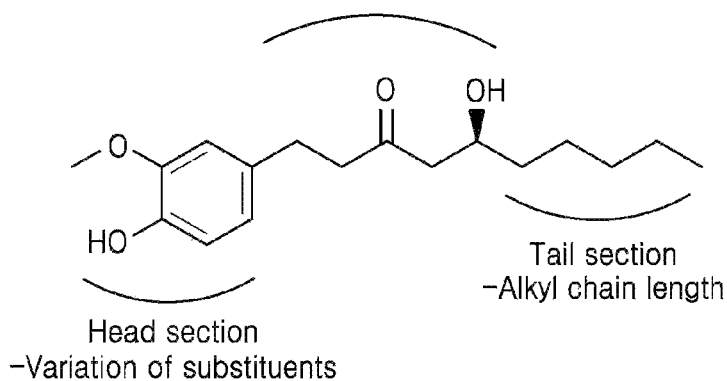
Middle section
- Rotational flexibility
- Necessity of OH group
- Absolute configuration
Tail section
-Alkyl chain length
Head section
-Variation of substituents

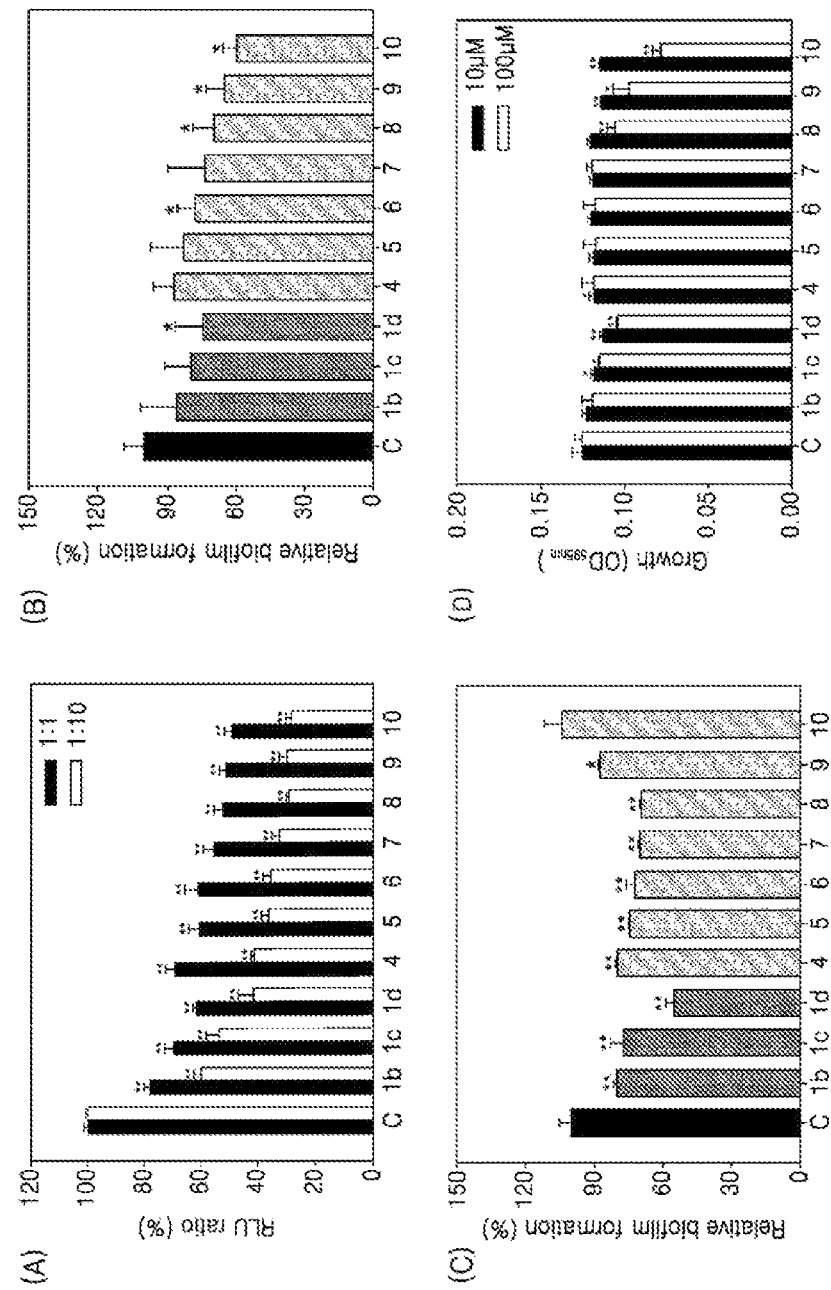
[Fig. 3]

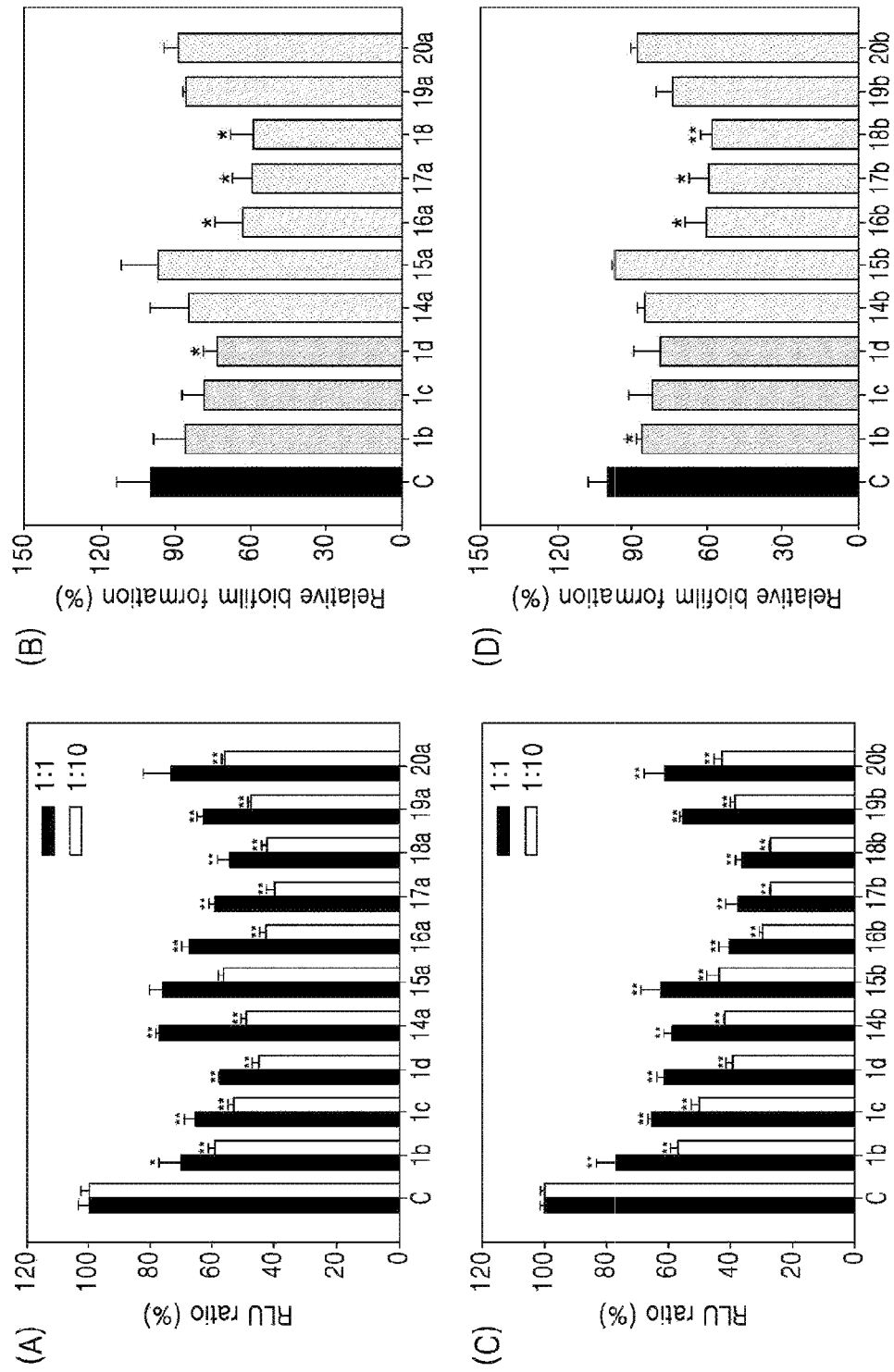
[Fig. 4]

[Fig. 5]
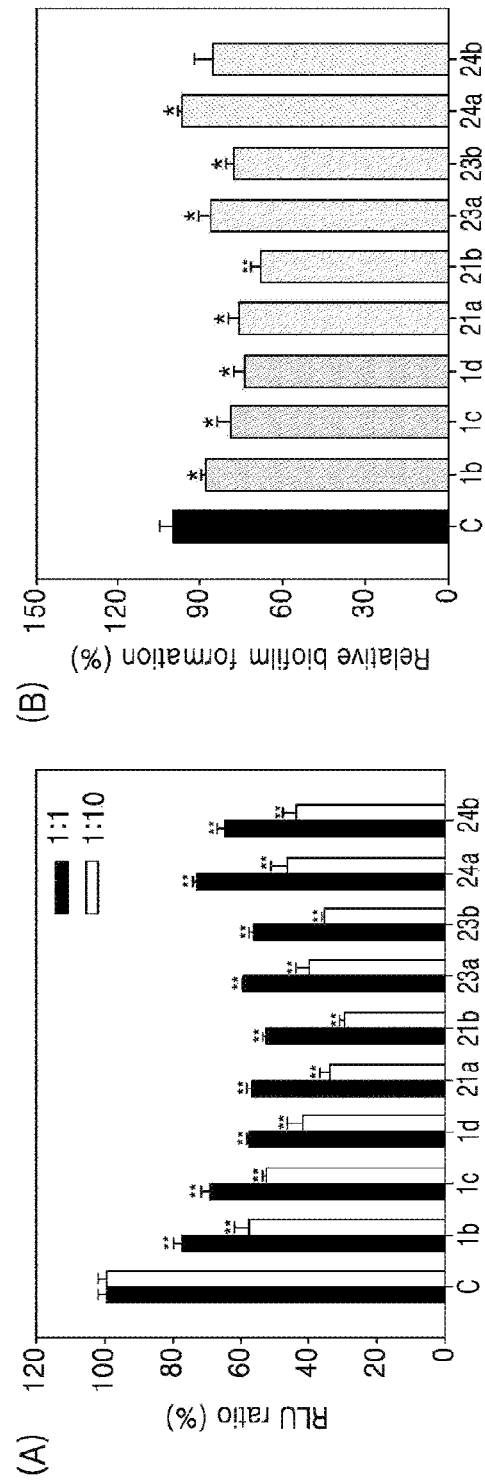

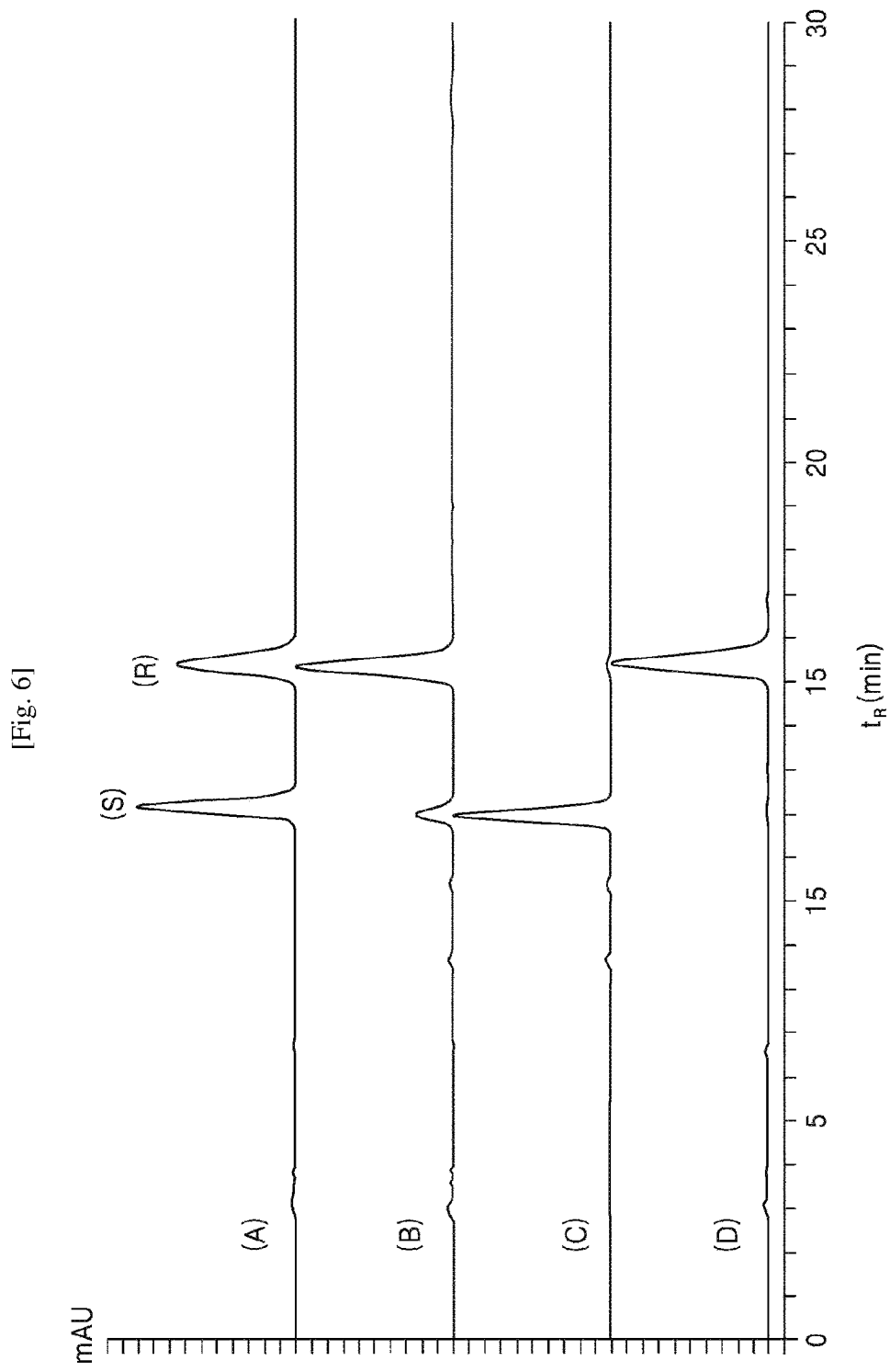

[Fig. 7]
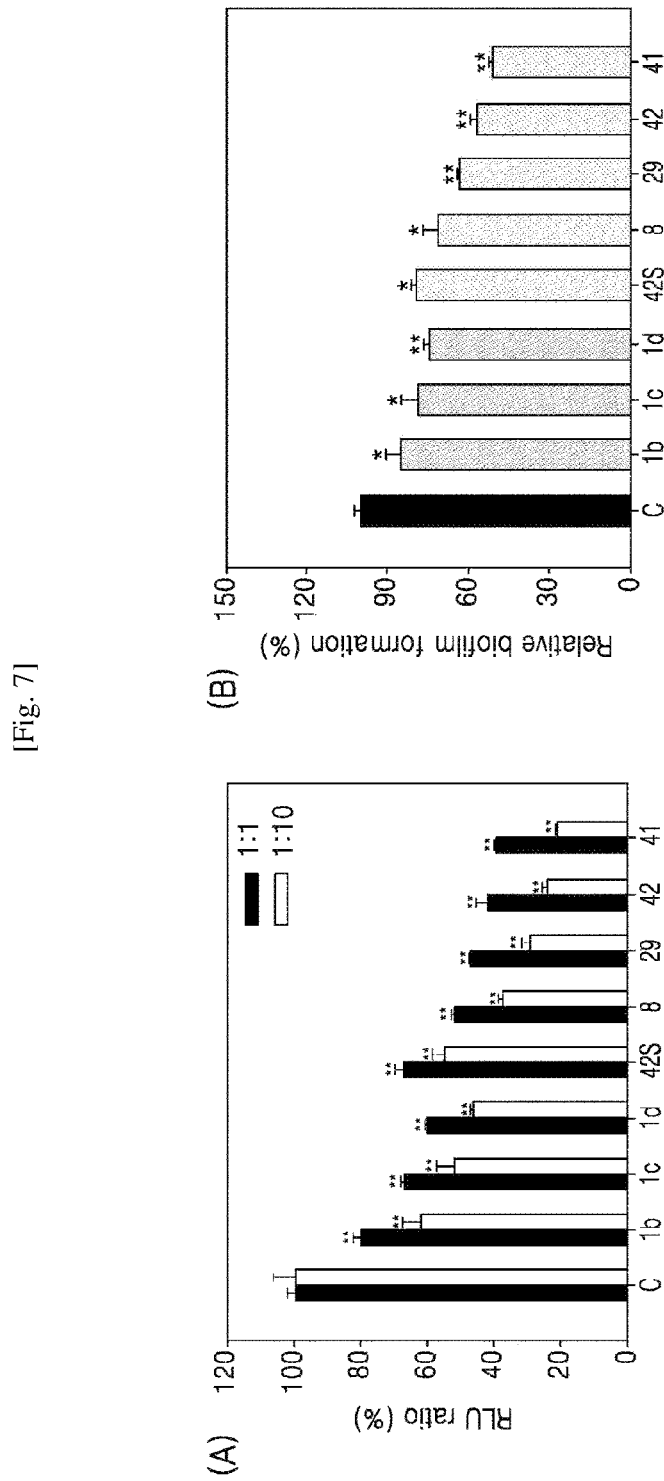

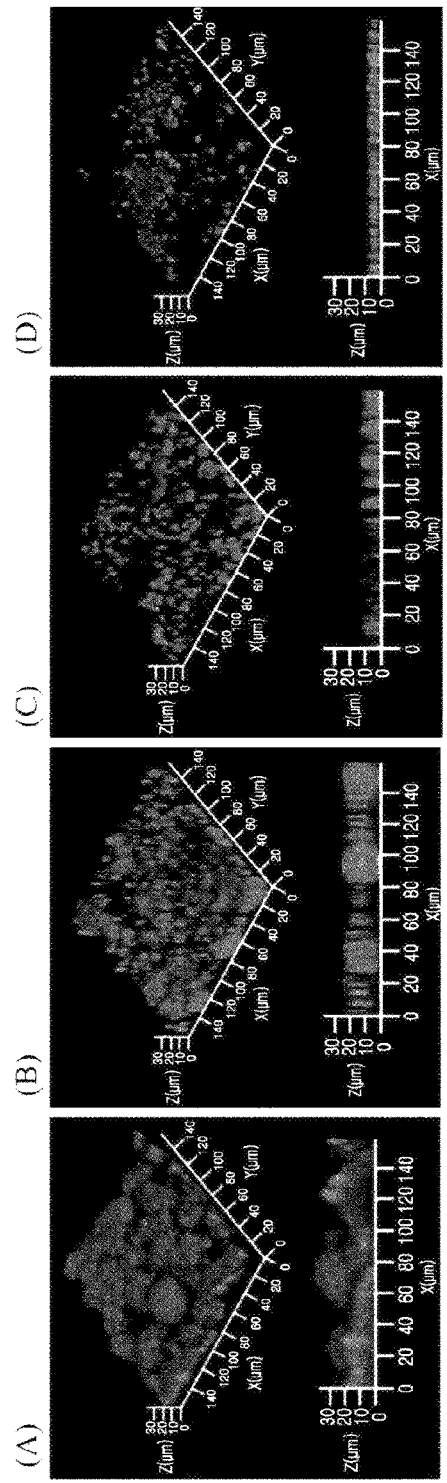

[Fig. 9]
(A)
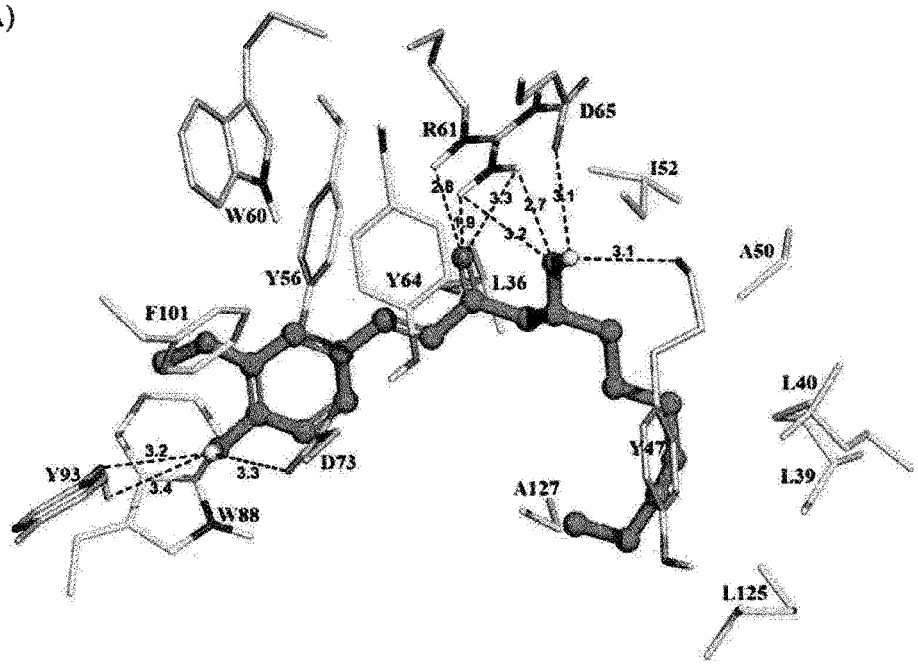
(B)
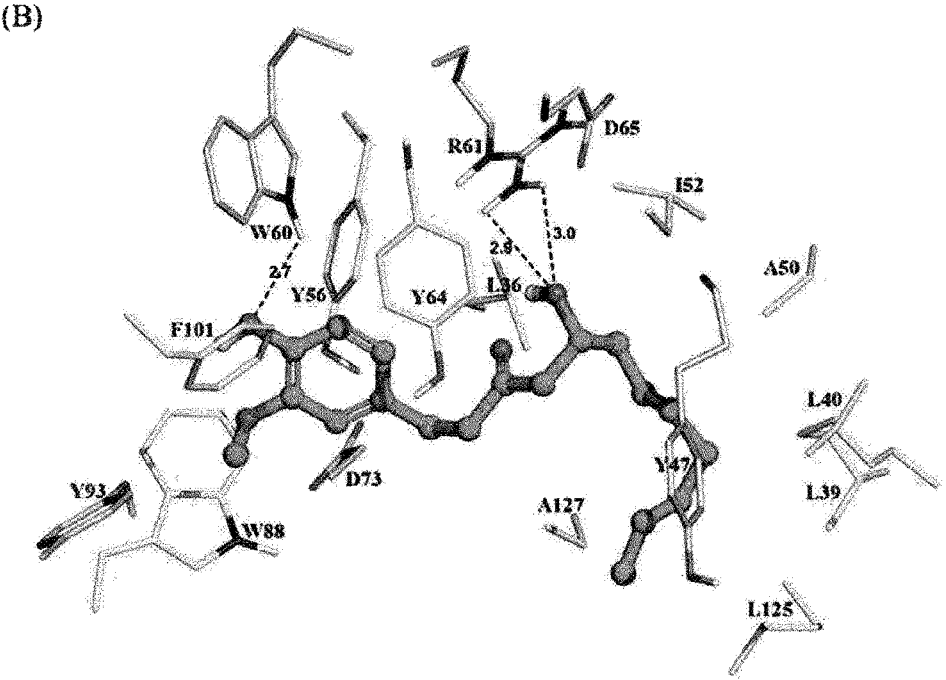

GINGEROL DERIVATIVE HAVING INHIBITORY ACTIVITY AGAINST BIOFILM FORMATION AND PHARMACEUTICAL COMPOSITION COMPRISING SAME AS EFFECTIVE INGREDIENT FOR PREVENTING OR TREATING BIOFILM-CAUSED INFECTION SYMPTOM

CROSS REFERENCE TO RELATED APPLICATIONS

This application is a U.S. National Stage Application of International Application No. PCT/KR2018/008171, filed on Jul. 19, 2018, which claims the benefit under 35 USC 119(a) and 365(b) of Korean Patent Application No. 10-2017-0092270, filed on Ju. 20, 2017, and Korean Patent Application No. 10-2018-0078859, filed on Jul. 6, 2018 in the Korean Intellectual Property Office, the entire disclosure of which is incorporated herein by reference for all purposes.

TECHNICAL FIELD

The present invention relates to a gingerol derivative having inhibitory activity against biofilm formation and a pharmaceutical composition for preventing or treating infections caused by biofilms including the gingerol derivative as an active ingredient.

BACKGROUND ART

Biofilms of microorganisms are their own lifestyle to adapt in the environment. Biofilms formed by microorganisms are difficult to remove due to their strong tendency to adhere to various surfaces. Biofilms are more difficult to disinfect and sterilize when adhered to surfaces due to their much better resistance to harsh environmental conditions (for example, pH, temperature, and nutrient depletion), antibiotic attack, etc. than when they are floating. Microorganisms exist in the form of biofilms in most natural and industrial environments because they can benefit from biofilm formation.

Biofilm-forming microorganisms are surrounded by self-secreted extracellular polymeric substances (EPSs, including carbohydrates, proteins, and nucleic acids), which can exist fixed to the surface. Accordingly, biofilms can be defined as communities of microorganisms (for example, bacteria, yeasts, and fungi) in the form of films that are adherent to the surfaces of parts of the human body (for example, skin, oral cavity, and teeth) and facilities (for example, pipelines and storage tanks) under specific conditions. Biofilms serve as places where microorganisms inhabit and also accelerate the inhabitation of bacteria. Such biofilm-forming microorganisms may cause serious problems in the industrial and medical sectors. Thus, more research needs to be conducted on compositions and methods for inhibiting biofilm formation.

*Pseudomonas aeruginosa* (*P. aeruginosa*) is an opportunistic pathogen that causes infections in people with a weakened immune system, e.g., patients with cystic fibrosis, chronic wounds, pneumonia, AIDS, sepsis, or cancer. It is one of the six most dangerous bacterial species according to the Infectious Diseases Society of America. In particular, *P. aeruginosa* infection is the main cause of mortality in patients with cystic fibrosis. *P. aeruginosa* can form a so-called biofilm and biofilm cells are embedded in a self-produced exopolysaccharide matrix that confers antibiotic resistance. Biofilms are involved in most of microbial infections of humans (~80% of such bacterial infections). Biofilms retard penetration of antibiotics and reduces the antibiotic activity, thus reducing treatment efficacy.

During biofilm formation, bacterial cells communicate with one another by means of quorum sensing (QS) network. QS is a cell-to-cell communication system in which bacteria release and recognize chemical signals (autoinducers), and QS enables bacteria to behave as a group to adapt to environmental changes. In general, Gram-negative bacteria including *P. aeruginosa* produce and release N-acylhomoserine lactone (AHL) as a QS signal molecule. The QS mechanism of *P. aeruginosa* is tightly regulated by the three main signal production and recognition systems: LasI-LasR, RhlI-RhlR, and PQS-MvfR. LasI in *P. aeruginosa* produces an extracellular diffusible N-(3-oxododecanoyl)-L-homoserine lactone (OdDHL, 1*a* in FIG. 1), which activates expression of genes responsible for group behaviors including biofilm formation and production of virulence factors. When OdDHL reaches a threshold concentration, the OdDHL-LasR complex binds to the promoter regions of multiple genes affecting RhlIRh1R and 2-heptyl-3-hydroxy-4(1H)-quinolone (PQS)-MvfR systems. Similarly, RhlI produces N-butyryl-L-homoserine lactone (BHL), which is recognized by the transcriptional regulator RhlR. In the PQS-MvfR system, PQS and its precursors bind to the transcriptional regulator MvfR, resulting in transcription of target genes. Among the three systems, LasI-LasR is considered to be a master regulator of QS networks and a key system in the biofilm formation by *P. aeruginosa*.

*P. aeruginosa* forms biofilms and produces virulence factors through QS pathways. Therefore, disruption of these signal production and recognition systems is an attractive strategy for attenuating the virulence of *P. aeruginosa*. One of the antivirulence approaches is to interrupt the interaction between chemical signals (e.g., OdDHL, BHL, and PQS) and their cognate receptors (e.g., LasR, RhlR, and MvfR). For instance, halogenated furanones from the marine alga *Delisea pulchra* have a structure similar to AHL and can bind to LasR by competing with OdDHL. In addition, (Z)-4-bromo-5-(bromomethylene)furan-2(5H)-one (furanone C-30, 1*d* in FIG. 1), a synthetic molecule, inhibits the expression of virulence factors by interfering with *P. aeruginosa* QS systems.

It was previously demonstrated that (S)-6-gingerol (1*b*, FIG. 1) reduces biofilm formation and production of virulence factors by competing with OdDHL for LasR of *P. aeruginosa*. RT-qPCR analyses revealed that (S)-6-gingerol reduces the expression of genes (e.g., las, rhl, pqs, and phz genes) in the QS system and suppresses the production of virulence factors (e.g., exoprotease, pyocyanin, and rhamnolipid), indicating that it interferes with the interaction between OdDHL and LasR, at the top of the hierarchical QS network tree of *P. aeruginosa*. Molecular modeling studies of the interaction of (S)-6-gingerol with LasR (PDB code 2UV0) indicates that the 3'-hydroxyl-4'-methoxyphenyl moiety engages in a hydrogen-bonding interaction with hydrophilic amino acids, while the alkyl side chain forms a hydrophobic bond.

Under the above-described background, the present inventors aimed to investigate the effect of each functional group of (S)-6-gingerol on LasR-binding affinity and on biofilm formation by *P. aeruginosa*, and as a result, found that 6- and 8-gingerol analogs synthesized based on the chemical structure of (S)-6-gingerol act as LasR antagonists and their inhibitory activities against biofilm formation are significantly improved. The present invention has been accomplished based on this finding.

DETAILED DESCRIPTION OF THE INVENTION

Problems to be Solved by the Invention

The present invention intends to provide a gingerol derivative having inhibitory activity against biofilm formation.

The present invention also intends to provide a composition for inhibiting biofilm formation including the gingerol derivative.

The present invention also intends to provide a pharmaceutical composition for preventing or treating infections caused by biofilms including the gingerol derivative or a pharmaceutically acceptable salt thereof as an active ingredient.

Means for Solving the Problems

The present invention provides a gingerol derivative represented by Formula 1:

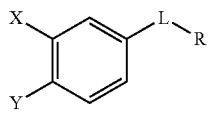

[Formula 1]

A description is given regarding the structure and specific substituents of

Formula 1 and specific examples of gingerol derivatives that can be represented by Formula 1.

The present invention also provides a composition for inhibiting biofilm formation including the gingerol derivative represented by Formula 1.

The present invention also provides a pharmaceutical composition for preventing or treating biofilm infections caused by biofilms including the gingerol derivative represented by Formula 1 or a pharmaceutically acceptable salt thereof as an active ingredient.

Effects of the Invention

The gingerol derivative of the present invention exhibits significantly improved binding affinity for LasR and inhibitory activity against biofilm formation. Therefore, the gingerol derivative of the present invention can act on various membrane surfaces where biofilms tend to form and can effectively inhibit the formation of the corresponding biofilms. In addition, the use of the pharmaceutical composition according to the present invention can fundamentally prevent or treat a variety of infections caused by biofilms due to the presence of the gingerol derivative in the pharmaceutical composition.

BRIEF DESCRIPTION OF THE DRAWINGS

FIG. 1 shows small molecules interacting with LasR of *P. aeruginosa*.

FIG. 2 shows a strategy for structural modification of gingerol derivatives.

FIG. 3 shows the effects of alkyl chain length variation in gingerol derivatives. DMSO (C, negative control) and compounds 1*b*, 1*c*, and 1*d* (positive controls) were used. (A) LasR binding activity of gingerol derivatives (compounds 4-10, Formulae 2-8) at different ratios of each of the gingerol derivatives (compound 4-10) to compound 1*a* (1:1 or 1:10). (B) Biofilm formation at 10 µM gingerol derivatives (compounds 4-10). (C) Biofilm formation with gingerol derivatives (compounds 4-10) at 100 µM. (D) Growth inhibition by gingerol derivatives (compounds 4-10) at 10 or 100 µM for 24 h. (**) P<0.005 and (*) P<0.05 as compared with the control. RLU ratio (%) in the Y axis is the relative luminescence unit ((luminescence/$OD_{595}$)×100).

FIG. 4 shows the effects of head group variation in 6- and 8-gingerol derivatives. DMSO (C, negative control) and compounds 1*b*, 1*c*, and 1*d* (positive controls) were used. (A) LasR binding activity of compounds 14*a*-20*a* (Formulae 9, 11, 13, 15, 17, 19, and 21) at different ratios of each of compounds 14*a*-20*a* to compound 1*a* (1:1 or 1:10). (B) Biofilm formation at 10 µM 6-gingerol derivatives (compounds 14*a*-20*a*). (C) LasR activity of compounds 14*b*-20*b* (Formulae 10, 12, 14, 16, 18, 20, and 22) at different ratios of each of compounds 14*b*-20*b* to compound 1*a*. (D) Biofilm formation at 10 µM 8-gingerol derivatives (compounds 14*b*-20*b*). (**) P<0.005 and (*) P<0.05 as compared with the control.

FIG. 5 shows the rotational flexibility and effect of the β-hydroxyl group on LasR-binding affinity and on inhibition of biofilm formation. DMSO (C, negative control) and compounds 1*b*, 1*c*, and 1*d* (positive controls) were used. (A) LasR binding activity of compounds 21*a*-24*b* (compounds 21*a*, 21*b*, 22*a*, and 22*b* correspond to Formulae 23, 24, 25, and 26, respectively) at different ratios of each of compounds 21*a*-24*b* to compound 1*a* (1:1 or 1:10). (B) Biofilm formation at 10 µM concentration of compounds 21*a*-24*b*. (**) P<0.005 and (*) P<0.05 as compared to the control.

FIG. 6 shows the chiral resolution of 8-gingerol: (A) compound 8 (Formula 6); (B) compound 29 (Formula 28); (C) compound 42S; (D) compound 42 (Formula 28).

FIG. 7 shows the effect of absolute configuration of 8-gingerol derivatives. DMSO (C, negative control) and compounds 1*b*, 1*c*, and 1*d* (positive controls) were used. (A) LasR binding activity of 8-gingerol derivatives (compounds 8, 29, 41, 42, and 42S) at different ratios of each of compounds 8, 29, 41, 42, and 42S to compound 1*a* (1:1 or 1:10)). (B) Biofilm formation of 8-gingerol derivatives (compounds 8, 29, 41, 42, and 42S) at 10 µM. (**) P<0.005 and (*) P<0.05 as compared to the control.

FIG. 8 shows confocal laser scanning microscopy (CLSM) images of *P. aeruginosa* biofilm formation. DMSO (negative control) and compound 1*c* (positive control) were used. (A) Biofilm formation in the presence of DMSO only. (B) Biofilm formation at 10 µM concentration of compound 1*c*. (C) Biofilm formation at 10 µM concentration of compound 42. (D) Biofilm formation at 10 µM concentration of compound 41. The biofilms were stained with ConA (carbohydrate, green) and Ruby (protein, red).

FIG. 9 shows (A) hydrogen-bonding interactions between compound 41 (Formula 27) and LasR (PDB code 2UV0) and (B) hydrogen-bonding interactions between compound 42 (Formula 28) and LasR. The hydrogen-bonding distance cutoff is 3.5 Å.

BEST MODE FOR CARRYING OUT THE INVENTION

The present invention will now be described in more detail. The present invention is directed to a gingerol derivative having inhibitory activity against biofilm formation, represented by Formula 1:

[Formula 1]

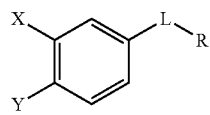

wherein X and Y are identical to or different from each other and are each independently selected from hydrogen, halo, hydroxy, amino, nitro, cyano, trifluoromethyl, and O—R' (wherein R' is $C_1$-$C_4$ alkyl), L is selected from $C_1$-$C_7$ alkylene and $C_2$-$C_7$ alkenylene, and R is represented by Structural Formula 1:

[Structural Formula 1]

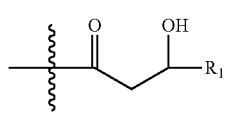

wherein $R_1$ is $C_1$-$C_{20}$ alkyl.

Specifically, the gingerol derivative represented by Formula 1 can be selected from, but not limited to, the derivatives represented by Formulae 2 to 28:

[Formula 2]

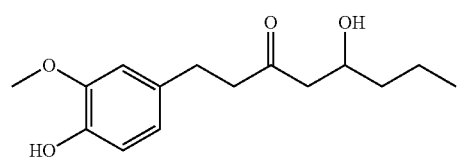

[Formula 3]

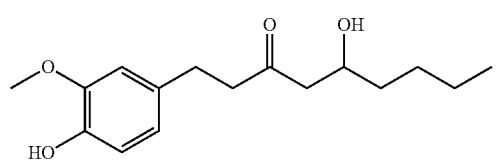

[Formula 4]

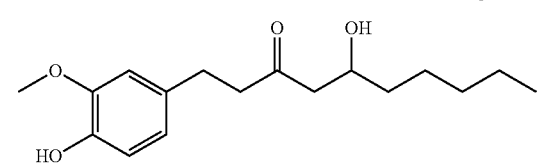

[Formula 5]

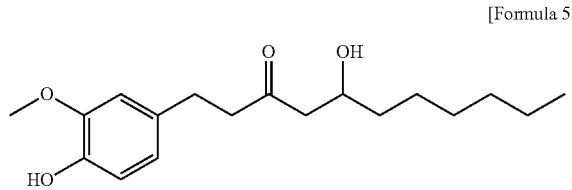

[Formula 6]

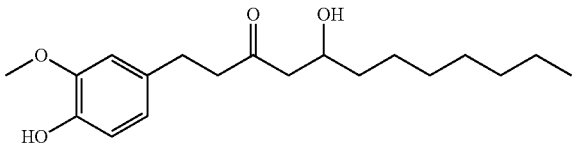

[Formula 7]

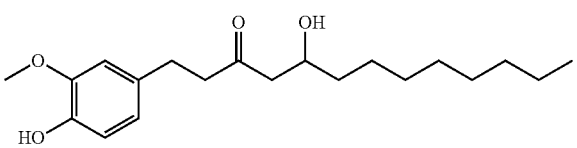

[Formula 8]

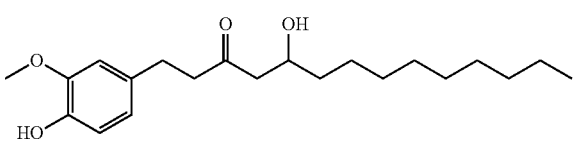

[Formula 9]

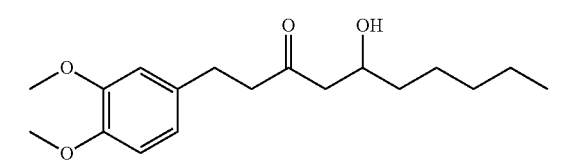

[Formula 10]

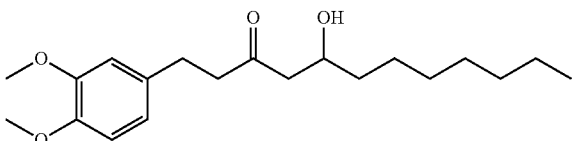

[Formula 11]

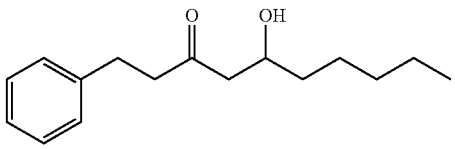

[Formula 12]

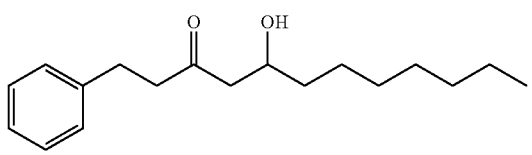

[Formula 13]

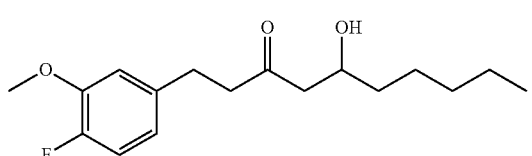

[Formula 14]

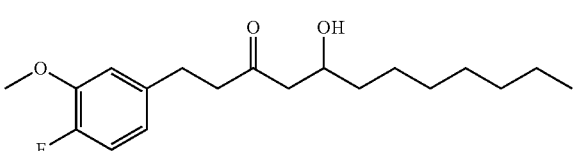

[Formula 15]
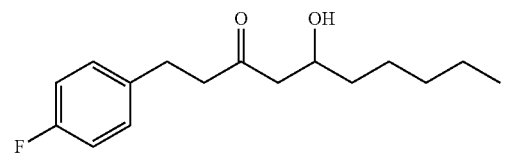

[Formula 16]
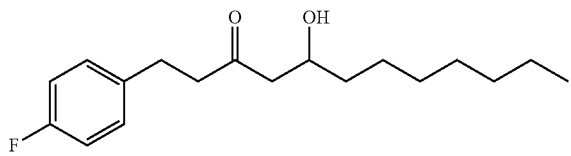

[Formula 17]
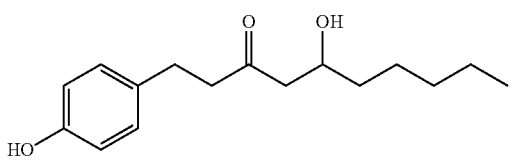

[Formula 18]
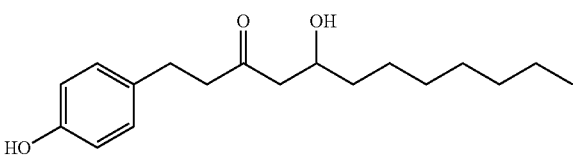

[Formula 19]
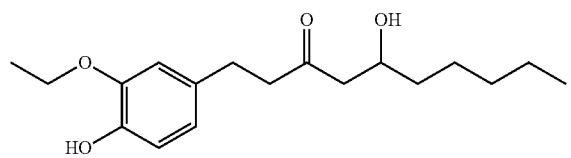

[Formula 20]
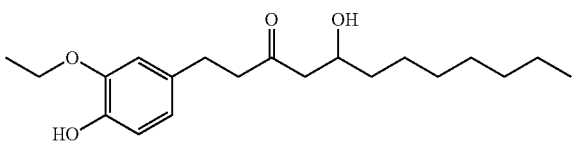

[Formula 21]
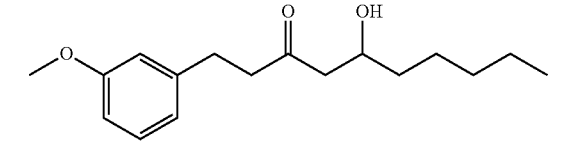

[Formula 22]
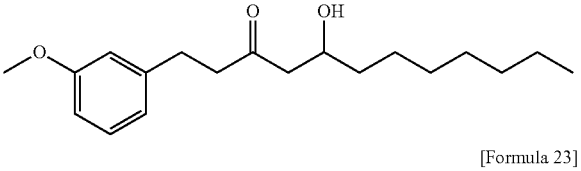

[Formula 23]
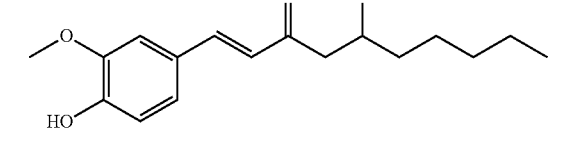

[Formula 24]
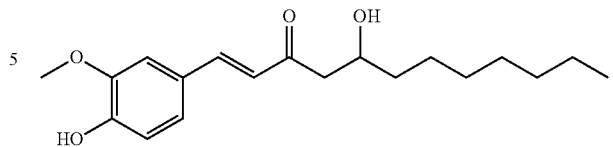

[Formula 25]
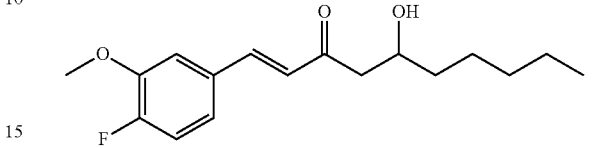

[Formula 26]
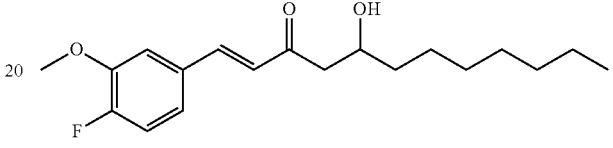

[Formula 27]
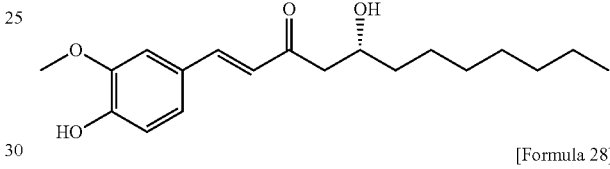

[Formula 28]
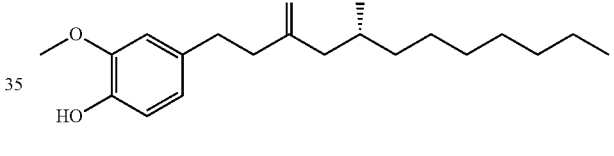

The biofilm may be formed by one or more bacterial species selected from the group consisting of *Pseudomonas aeruginosa*, *Salmonella* spp., *Shigella* spp., *Vibrio parahaemolyticus*, *Vibrio choreae*, *Escherichia coli* O-157, *Campylobacter jejuni*, *Clostridium difficile*, *Clostridium perfringens*, *Yersinia enterocolitica*, *Helicobacter pylori*, *Entemoeba histolytica*, *Bacillusu cereus*, *Clostridium botulinum*, *Haemophilus influenzae*, *Streptococcus pneumoniae*, *Chlamidia pneumoniae*, *Legionella pneumoniae*, *Branhamella catarrhalis*, *Mycobacterium tuberculosis*, *Mycoplasma pneumoniae*, *Storeptcoccus pyogenes*, *Corynebacterium diphtherias*, *Bordetella pertussis*, *Chramidia psittaci*, methicillin resistant *Staphylococcus aureus* (MRSA), *Escherichia coli*, *Klebsiella pneumoniae*, *Enterobacter* spp., *Proteus* spp., *Acinetobacter* spp., *Enterococcus faecalis*, *Staphylococcus saprophyticus*, and *Storeptcoccus agalactiae*.

The gingerol derivatives of Formulae 2 to 28 can be prepared according to the following synthetic procedures. Specifically, Scheme 1 shows a schematic synthetic procedure for the preparation of the gingerol derivatives represented by Formulae 2 to 8, Scheme 2 shows a schematic synthetic procedure for the preparation of the gingerol derivatives represented by Formulae 9 to 22, Scheme 3 shows a schematic synthetic procedure for the preparation of the gingerol derivatives represented by Formulae 23 to 26, Scheme 4 shows a schematic synthetic procedure for the preparation of the gingerol derivatives represented by Formulae 27 and 28 using D-proline as a catalyst, and Scheme 5 shows a schematic synthetic procedure for the preparation of the gingerol derivatives represented by Formulae 27 and 28 using Salen's catalyst.

[Scheme 1]

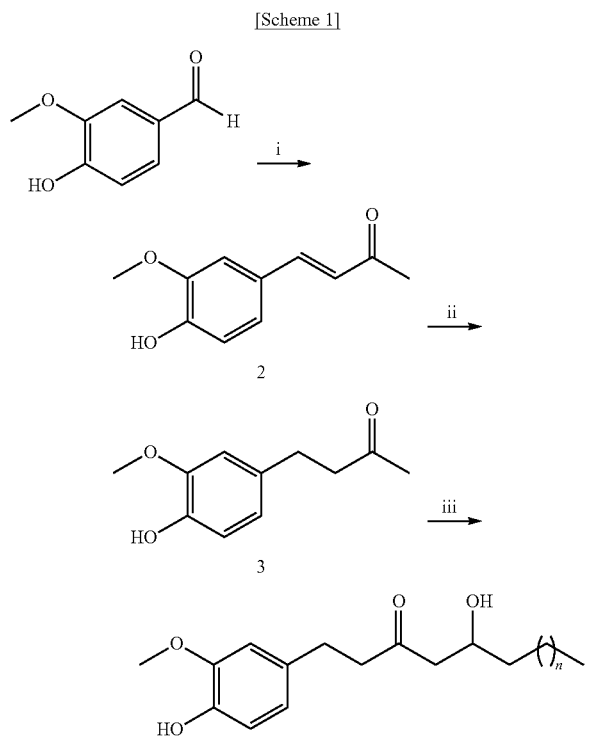

4: n = 1
5: n = 2
6: n = 3
7: n = 4
8: n = 5
9: n = 6
10: n = 7

(Reagents and conditions: (i) 10% NaOH, acetone, room temperature, 16 h, 71%; (ii) H$_2$, Pd/C, MeOH, room temperature, 2 h, 97%; (iii) LDA, aldehydes, THF, -78° C., 2 h, 30-47%)

[Scheme 2]

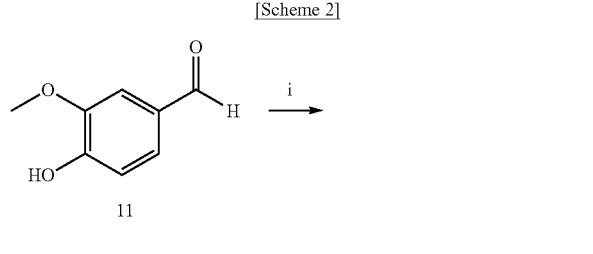

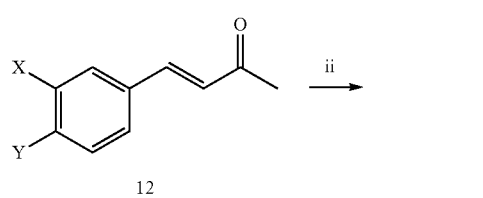

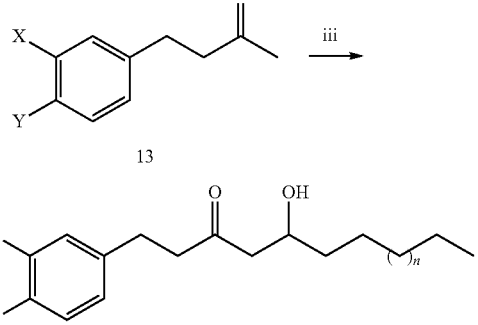

14a: n = 1, X = OMe, Y = OMe
14b: n = 3, X = OMe, Y = OMe
15a: n = 1, X = H, Y = H
15b: n = 3, X = H, Y = H
16a: n = 1, X = OMe, Y = F
16b: n = 3, X = OMe, Y = F
17a: n = 1, X = H, Y = F
17b: n = 3, X = H, Y = F
18a: n = 1, X = H, Y = OH
18b: n = 3, X = H, Y = OH
19a: n = 1, X = OEt, Y = OH
19b: n = 3, X = OEt, Y = OH
20a: n = 1, X = OMe, Y = H
20b: n = 3, X = OMe, Y = H (Reagents and conditions: (i) acetone, 10% NaOH, room temperature, 48 h, 35-75%; (ii) H$_2$, Pd/C, MeOH, room temperature, 2 h, 80-97%;; (ii) LDA, hexanal (n = 1) or octanal (n = 3), THF, -78° C., 2 h, 25-47%)

[Scheme 3]

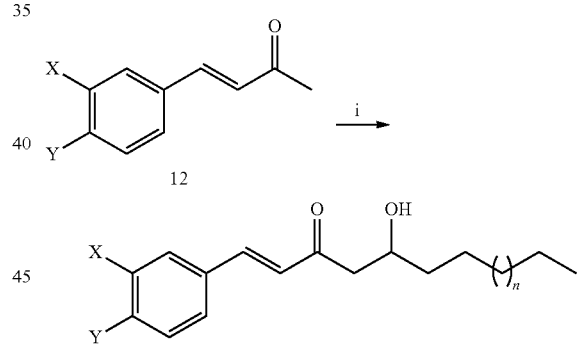

21a: n = 1, X = OMe, Y = OH
21b: n = 3, X = OMe, Y = OH
22a: n = 1, X = OMe, Y = F
22b: n = 3, X = OMe, Y = F

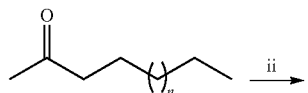

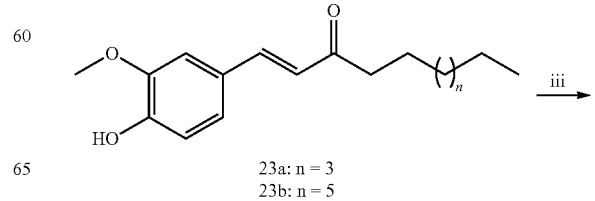

23a: n = 3
23b: n = 5

-continued

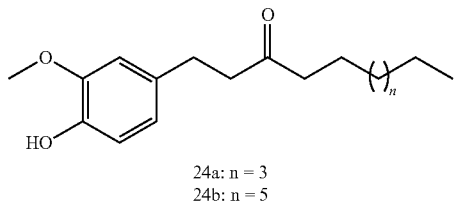

24a: n = 3
24b: n = 5

(Reagents and conditions: (i) LDA, hexanal (n = 1) or octanal (n = 3), THF, -78° C., 1 h, 30-35%; (ii) (L)-proline, vanillin, TEA, MeOH, room temperature, 48 h, 45-60%; (iii) H₂, Pd/C, MeOH, room temperature, 2 h 80-97%)

[Scheme 4]

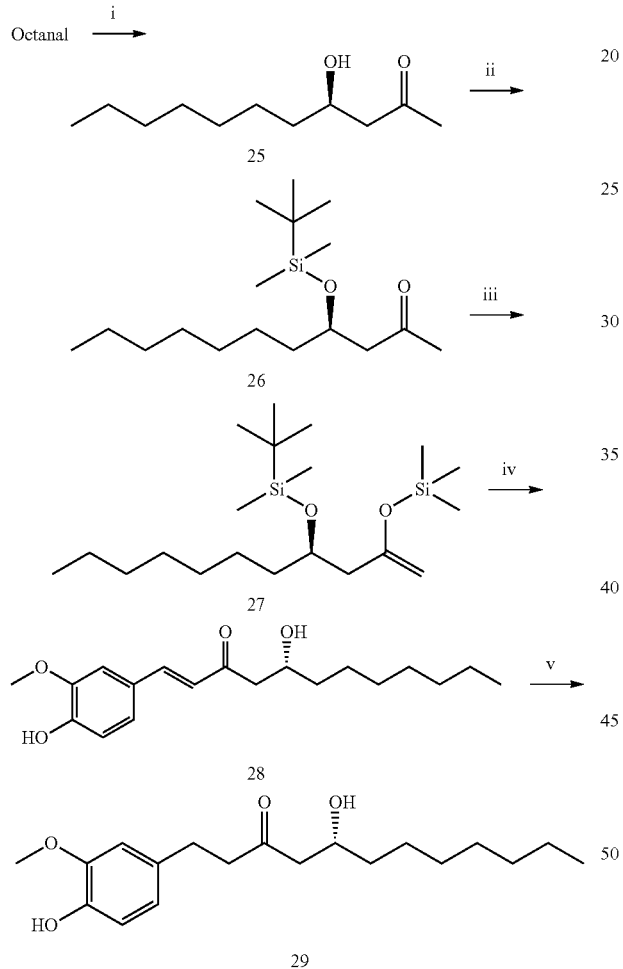

(Reagents and conditions: (i) acetone, (D)-proline, room temperature, 48 h, 48%; (ii) TBDMSCl, imidazole, CH₂Cl₂, room temperature, 10 h, 87%; (iii) TMSOTf, DIPEA, CH₂Cl₂, 0° C., 4 h; (iv) vanillin, BF₃·OEt₂, TEA, CH₂Cl₂, 0° C., 2 h (65% over 2 steps); (v) H₂, Pd/C, MeOH, room temperature, 2 h, 97%)

[Scheme 5]

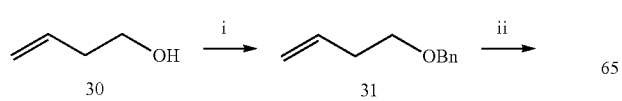

-continued

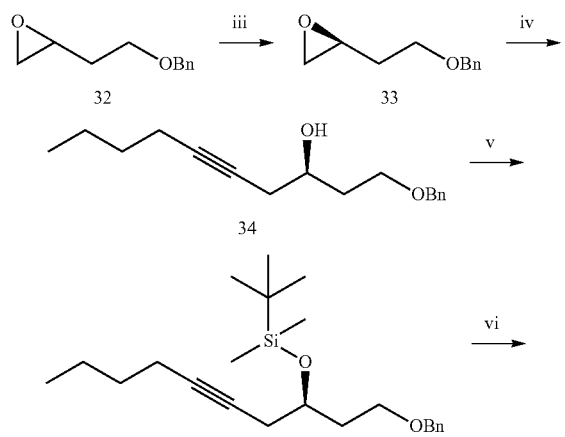

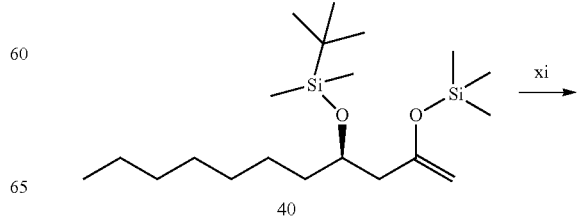

-continued

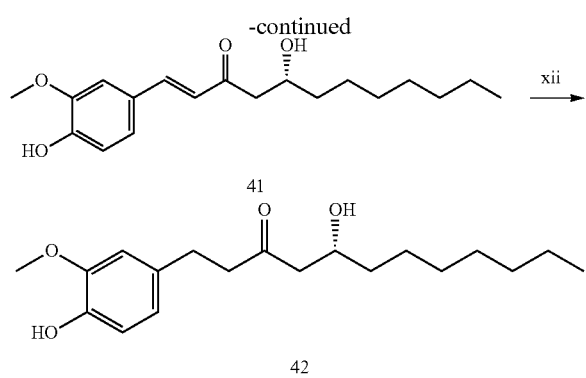

(Reagents and conditions: (i) NaH, BnBr, THF, 0° C. to room temperature, 16 h, 90%; (ii) m-CPBA, NaHCO₃, CH₂Cl₂, 0° C. to room temperature, 14 h, 72%; (iii) (N,N'-bis(3,5-di-tert-butylsalicylidene)-1,2-cyclohexanediaminocobalt(II), AcOH, H₂O, THF, 0° C. to room temperature, 16 h, 50%; (iv) hex-1-yne, n-BuLi, BF₃•OEt₂, THF, -78° C., 2 h, 57%; (v) TBDMSCl, imidazole, CH₂Cl₂, room temperature, 10 h, 87%; (vi) H₂, Pd/C, MeOH, room temperature, 2 h, 89%; (vii) NaIO₄, Ru(III)Cl₃, EtOAc, CH₃CN, H₂O, room temperature, 4 h, 67%; (viii) N,O-dimethylhydroxylamine•HCl, HOBt, EDC, DIPEA, THF, room temperature, 8 h, 93%; (ix) CH₃MgBr, THF, -78° C., 3 h, 90%; (x) TMSOTf, DIPEA, CH₂Cl₂, 0° C., 4 h; (xi) vanillin, BF₃•OEt₂, TEA, CH₂Cl, 0° C., 2 h (65% in two steps); (xii) H₂, Pd/C, MeOH, room temperature, 2 h, 97%)

The present invention is also directed to a composition for inhibiting biofilm formation including the gingerol derivative represented by Formula 1.

The present invention is also directed to a pharmaceutical composition for preventing or treating infections caused by biofilms including the gingerol derivative or a pharmaceutically acceptable salt thereof as an active ingredient.

The compound represented by Formula 1 may be used in the form of a pharmaceutically acceptable salt thereof and may be prepared into a formulation that does not impair the biological activity and physical properties of the compound without causing serious irritation in organisms when administered. The pharmaceutically acceptable salt may be obtained by reaction of the compound represented by Formula 1 with an inorganic acid such as hydrochloric acid, hydrobromic acid, sulfuric acid, nitric acid or phosphoric acid, a sulfonic acid such as methanesulfonic acid, ethanesulfonic acid or p-toluenesulfonic acid, or an organic carboxylic acid such as tartaric acid, formic acid, citric acid, acetic acid, trichloroacetic acid, trifluoroacetic acid, capric acid, isobutanoic acid, malonic acid, succinic acid, phthalic acid, gluconic acid, benzoic acid, lactic acid, fumaric acid, maleic acid or salicylic acid. The pharmaceutically acceptable salt may also be obtained by reaction of the compound represented by Formula 1 with a base. In this case, the pharmaceutically acceptable salt may be an ammonium salt, an alkali metal salt such as a sodium or potassium salt, an alkaline earth metal salt such as a calcium or magnesium salt, a salt with an organic base such as dicyclohexylamine, N-methyl-D-glucamine or tris(hydroxymethyl)methylamine or a salt with an amino acid such as arginine or lysine.

The compound represented by Formula 1 is intended to include all salts, hydrates, and solvates thereof that can be prepared by suitable methods known in the art, as well as the pharmaceutically acceptable salt thereof.

The infections caused by biofilms may be infections that can be inhibited by antibacterial agents and may include those that have been treated with existing antiseptics and antibiotics and those that can be caused during disease diagnosis. Examples of the infections caused by biofilms include cystic fibrosis, pneumonia, dental caries, periodontitis, otitis media, musculoskeletal infections, necrotizing fasciitis, biliary tract infection, osteomyelitis, bacterial prostatitis, native valve endocarditis, melioidosis, nosocomial infection, ICU pneumonia, urinary catheter cystitis, peritoneal dialysis (CAPD) peritonitis, and biliary stent blockage.

Biofilm formation can affect sutures, exit sites, arteriovenous sites, scleral buckles, contact lenses, IUDs, endotracheal tubes, Hickman catheters, central venous catheters, mechanical heart valves, vascular grafts, orthopedic devices, penile prostheses. Further applications are described in Costerton J et al. and Costerton J and Steward (2001 Battling Biofilms, Scientific American pp 75-81), the disclosures of which are incorporated herein by reference. Other locations at which biofilms may form include dental plaque which may lead to gum disease and cavities, contact lenses which may lead to eye infections, ears which may lead to chronic infection, and lungs which may lead to pneumonia.

The infection may be cystic fibrosis, which can result from skin infection, burn infection and/or wound infection. The composition of the invention may be particularly suitable for the treatment of infection in immunocompromised individuals.

Biofilm formation may be caused by pathogens. The term "pathogens" refers to microorganisms, including, but not limited to, bacteria and viruses that cause diseases, particularly causal bacteria of intestinal infections, respiratory infections, and urinary tract infections. Specific examples of such causal bacteria include *Pseudomonas aeruginosa*, *Salmonella* spp., *Shigella* spp., *Vibrio parahaemolyticus*, *Vibrio choreae*, *Escherichia coli* O-157, *Campylobacter jejuni*, *Clostridium difficile*, *Clostridium perfringens*, *Yersinia enterocolitica*, *Helicobacter pylori*, *Entemoeba histolytica*, *Bacillusu cereus*, *Clostridium botulinum*, *Haemophilus influenzae*, *Streptococcus pneumoniae*, *Chlamidia pneumoniae*, *Legionella pneumoniae*, *Branhamella catarrhalis*, *Mycobacterium tuberculosis*, *Mycoplasma pneumoniae*, *Storeptcoccus pyogenes*, *Corynebacterium diphtherias*, *Bordetella pertussis*, *Chramidia psittaci*, methicillin resistant *Staphylococcus aureus* (MRSA), *Escherichia coli*, *Klebsiella pneumoniae*, *Enterobacter* spp., *Proteus* spp., *Acinetobacter* spp., *Enterococcus faecalis*, *Staphylococcus saprophyticus*, and *Storeptcoccus agalactiae*.

The pharmaceutical composition of the present invention may include one or more known active ingredients that have prophylactic or therapeutic effects on infections caused by biofilms, together with the gingerol derivative of Formula 1. For administration, the composition of the present invention may further include one or more pharmaceutically acceptable carriers in addition to the active ingredient described above. Suitable pharmaceutically acceptable carriers include physiological saline, sterile water, Ringer's solution, buffered saline, dextrose solution, maltodextrin solution, glycerol, and ethanol. These pharmaceutically acceptable carriers may be used alone or as a mixture thereof. If necessary, the composition of the present invention may further include one or more additives selected from those well known in the art, for example, antioxidants, buffer solutions, and bacteriostatic agents. The composition of the present invention may be formulated with diluents, dispersants, surfactants, binders and lubricants to prepare injectables such as aqueous solutions, suspensions or emulsions, pills, capsules, granules or tablets. The pharmaceutical composition of the present invention can be formulated according to the type of diseases or the kind of ingredients in accordance with any suitable method known in the art, preferably, any of the methods disclosed in Remington's Pharmaceutical Science (Mack Publishing Company, Easton PA.).

The composition of the present invention may be administered orally or parenterally depending on intended methods. The dosage may vary depending on the body weight, age, sex, health and diet of subjects to be treated, the time and mode of administration, the rate of excretion, the severity of disease, and other relevant factors. The composition is administered in an amount such that the daily dose of the gingerol derivative of Formula 1 ranges from 0.5 to 30 mg/kg, preferably from about 10 to about 20 mg/kg. The daily dose may be increased or decreased depending on clinical results and is preferably administered in a single dose or in divided doses several times per day.

For effective prevention or treatment of infections caused by biofilms, the composition of the present invention may be used alone or in combination with an antiseptic, an antibiotic, a hormonal therapeutic agent, a therapeutic drug and/or a biological response modulator known in the art.

As used herein, the term "prevent" or "preventing" refers to inhibiting a disease or disorder from occurring in an animal or human that may be predisposed to the disease or disorder but has not yet been diagnosed as having it. As used herein, the term "treat" or "treating" refers to inhibiting the development of a disease or disorder or ameliorating or eliminating the disease or disorder.

As used herein, the term "including as an active ingredient" means the presence of the corresponding ingredient in an amount necessary or sufficient to achieve a desired biological effect. In real applications, the active ingredient is used in a therapeutically effective amount to treat a target disease and such an amount can suitably be determined taking into consideration other toxicities caused by the active ingredient. For example, the amount of the active ingredient may vary depending on various factors, such as the disease or condition to be treated, the dosage form of the composition, the size of a subject or the severity of the disease or condition. The effective amount of the composition can be empirically determined by those skilled in the art without excessive experiments.

Other terms and abbreviations used herein may be understood as their meanings recognized generally by those skilled in the art, unless otherwise defined.

Mode for Carrying out the Invention

The present invention will be explained in more detail with reference to the following examples. However, these examples are provided to assist in understanding the invention and are not intended to limit the scope of the present invention.

EXPERIMENTAL METHOD

Experimental Materials and General Procedures

All the chemicals and solvents used in the reaction were purchased from Sigma-Aldrich, TCI, or Alfa Aesar and were used without further purification. Reactions were monitored by TLC on 0.25 mm Merck precoated silica gel plates (60 F254). Reaction progress was monitored by TLC analysis using a UV lamp and/or $KMnO_4$ staining for detection purposes. Column chromatography was performed on silica gel (230-400 mesh, Merck, Darmstadt, Germany). NMR spectra were recorded at room temperature on either Bruker BioSpin Avance 300 MHz NMR or Bruker Ultrashield 600 MHz Plus spectrometer. Chemical shifts are reported in parts per million (ppm, δ) with TMS as an internal standard. Coupling constant are given in hertz. $^{13}C$ NMR spectra were obtained by using the same NMR spectrometers and were calibrated with $CDCl_3$ (δ=77.16 ppm). Mass spectra were obtained on a Shimadzu (MALDI-TOF) mass spectrometer or an Agilent 6530 Accurate mass Q-TOF LC/MS spectrometer or an electrospray ionization PE Biosystems Sciex Api 150 EX mass spectrometer single quadruple equipped with a turbo ion spray interface. The purity of all final compounds was measured by analytical reverse phase HPLC on an Agilent 1260 Infinity (Agilent) with a C18 column (Phenomenex, 150 mm×4.6 mm, 3 μm, 110 Å). RP-HPLC was performed using the following isocratic conditions: for method A, mobile phase was acetonitrile and water (50:50, v/v); for method B, mobile phase was acetonitrile and water (55:45, v/v); for method C, mobile phase was acetonitrile and water (70:30, v/v). All compounds were eluted with a flow rate of 0.7 mL/min and monitored at UV detector: 254 nm. Purity of the tested compounds was >95%.

Synthesis of Compounds

Synthesis of Compound 2 ((E)-4-(4-Hydroxy-3-methoxyphenyl)but-3-en-2-one)

To a solution of 4-hydroxy-3-methoxybenzaldehyde (1.25 g, 8.2 mmol) in acetone (50 mL) was added 10% NaOH (3.28 mL, 8.2 mmol) dropwise. The reaction mixture was stirred at 25° C. for 48 h and then was quenched with water and extracted with EtOAc. The organic layer was dried over $MgSO_4$, filtered, and concentrated under reduced pressure. The crude residue was purified by column chromatography on silica gel (eluting with a mixture of hexane-EtOAc, 10:1 to 3:1) to furnish compound 2 (1.20 g, 71%) as yellow oil. $R_f$=0.25 (hexane/EtOAc=4:1, v/v).

Synthesis of Compound 3
(4-(4-Hydroxy-3-methoxyphenyl)butan-2-one)

To a solution of compound 2 (1.2 g, 6.2 mmol) in MeOH (20 mL) was added 10% Pd/C (200 mg, 0.187 mmol). The solution was then stirred in an atmosphere of $H_2$ gas for 4 h. The reaction mixture was filtered through a Celite pad and concentrated under reduced pressure. The crude residue was purified by column chromatography on silica gel (hexane/EtOAc=5:1, v/v) to furnish compound 3 (1.17 g, 97%) as colorless oil.

Synthesis of Compound 4 (5-Hydroxy-1-(4-hydroxy-3-methoxyphenyl)octan-3-one, Formula 2)

To a solution of compound 3 (200 mg, 1.0 mmol) in THF (5 mL) was added LDA (2.30 mL, 2.2 mmol) dropwise at −78° C. The solution was stirred for 1 h at the same temperature. Butanal (0.74 mL, 8.3 mmol) was then added dropwise. The reaction mixture was stirred for 3 h at the same temperature, quenched with aqueous $NH_4Cl$ (10 mL), and extracted with EtOAc. The organic layer was washed with brine, dried over $MgSO_4$, filtered, and concentrated under reduced pressure. The crude residue was purified by column chromatography on silica gel (toluene/EtOAc=10:1 to 5:1, v/v) to furnish compound 4 (15 mg, 13%) as colorless oil.

$^1H$ NMR (300 MHz, $CDCl_3$) δ6.85 (d, J=7.8 Hz, 1H), 6.69 (s, 1H), 6.66 (d, J=8.7 Hz, 1H), 5.51 (s, 1H), 4.06 (brs, 1H), 3.89 (s, 3H), 2.96 (brs, 1H), 2.86 (t, J=6.9 Hz, 2H), 2.75 (t, J=6.9 Hz, 2H), 2.54 (t, J=6.6 Hz, 2H), 1.51-1.27 (m, 4H), 0.93 (t, J=6.6 Hz, 3H); $^{13}C$ NMR (75 MHz, $CDCl_3$) δ211.5, 146.4, 143.9, 132.6, 120.7, 114.4, 110.9, 67.4, 55.9, 49.4, 45.5, 38.6, 29.3, 24.0, 18.7, 14.0. MS (MALDI-TOF) m/z calculated for $C_{15}H_{22}O_4^+[M]^+$, 266.2; found, 266.1. >98% purity (as determined by RP-HPLC, method B, $t_R$=3.49 min).

Synthesis of Compound 5 (5-Hydroxy-1-(4-hydroxy-3-methoxyphenyl)nonan-3-one, Formula 3)

Compound 5 was prepared in 32% yield as colorless oil, following the same procedure as described for the synthesis of compound 4 but with pentanal instead of butanal. $R_f$=0.15 (toluene/EtOAc=5:1, v/v).

$^1$H NMR (300 MHz, CDCl$_3$) δ6.84 (d, J=8.1 Hz, 1H), 6.69 (s, 1H), 6.68 (d, J=9.0 Hz, 1H), 5.50 (s, 1H), 4.04 (brs, 1H), 3.89 (s, 3H), 2.80 (s, 1H), 2.83 (t, J=6.6 Hz, 2H), 2.75 (t, J=6.6 Hz, 2H), 2.72-2.42 (m, 2H), 1.55-1.23 (m, 6H), 0.91-0.89 (m, 3H); $^{13}$C NMR (75 MHz, CDCl$_3$) δ211.5, 146.4, 143.9, 132.6, 120.7, 114.3, 110.9, 67.6, 55.8, 49.3, 45.4, 36.1, 29.3, 27.6, 22.6, 14.1. MS (MALDI-TOF) m/z calculated for $C_{16}H_{24}O_4^+[M]^+$, 280.2; found, 280.1. >98% purity (as determined by RP-HPLC, method B, $t_R$=4.20 min).

Synthesis of Compound 6 (5-Hydroxy-1-(4-hydroxy-3-methoxyphenyl)decan-3-one, Formula 4)

Compound 6 was prepared in 47% yield as colorless oil, following the same procedure as described for the synthesis of compound 4 but with hexanal instead of butanal. $R_f$=0.14 (toluene/EtOAc=5:1, v/v).

$^1$H NMR (300 MHz, CDCl$_3$) δ6.84 (d, J=7.8 Hz, 1H), 6.69 (s, 1H), 6.68 (d, J=8.7 Hz, 1H), 5.52 (s, 1H), 4.04 (brs, 1H), 3.89 (s, 3H), 2.96 (s, 1H), 2.85 (t, J=6.6 Hz, 2H), 2.75 (t, J=6.6 Hz, 2H), 2.68-2.43 (m, 2H), 2.68-2.43 (m, 8H), 0.98-0.81 (m, 3H); $^{13}$C NMR (75 MHz, CDCl$_3$) δ211.5, 146.4, 144.0, 132.6, 120.7, 114.4, 110.1, 67.7, 55.9, 49.4, 45.5, 36.4, 31.7, 29.3, 25.1, 22.6, 14.0. MS (MALDI-TOF) m/z calculated for $C_{17}H_{26}O_4^+[M]^+$, 294.2; found, 294.1. >98% purity (as determined by RP-HPLC, method B, $t_R$=5.30 min).

Synthesis of Compound 7 (5-Hydroxy-1-(4-hydroxy-3-methoxyphenyl)undecan-3-one, Formula 5)

Compound 7 was prepared in 28% yield as colorless oil, following the same procedure as described for the synthesis of compound 4 but with heptanal instead of butanal. $R_f$=0.15 (toluene/EtOAc=5:1, v/v).

$^1$H NMR (300 MHz, CDCl$_3$) δ6.85 (d, J=7.8 Hz, 1H), 6.69 (s, 1H), 6.68 (d, J=8.7 Hz, 1H), 5.50 (brs, 1H), 3.89 (s, 3H), 2.96 (brs, 1H), 2.86 (t, J=6.6 Hz, 2H), 2.75 (t, J=6.6 Hz, 2H), 2.72-2.41 (m, 2H), 1.71-1.21 (m, 10H), 0.98-0.89 (m, 3H); $^{13}$C NMR (75 MHz, CDCl$_3$) δ211.5, 146.4, 144.0, 132.7, 120.7, 114.4, 110.9, 67.7, 55.9, 49.4, 45.5, 36.5, 31.8, 29.3, 29.2, 25.4, 22.6, 14.1. MS (MALDI-TOF) m/z calculated for $C_{18}H_{28}O_4^+[M]^+$, 308.2; found, 308.2. >98% purity (as determined by RP-HPLC, method B, $t_R$=6.97 min).

Synthesis of Compound 8 (5-Hydroxy-1-(4-hydroxy-3-methoxyphenyl)dodecan-3-one, Formula 6)

Compound 8 was prepared in 32% yield as colorless oil, following the same procedure as described for the synthesis of compound 4 but with octanal instead of butanal. $R_f$=0.15 (toluene/EtOAc=5:1, v/v).

$^1$H NMR (300 MHz, CDCl$_3$) δ6.83 (d, J=8.1 Hz, 1H), 6.68 (s, 1H), 6.66 (d, J=9.0 Hz, 1H), 5.52 (s, 1H), 4.02 (brs, 1H), 3.87 (s, 3H), 2.95 (s, 1H), 2.84 (t, J=6.9 Hz, 2H), 2.73 (t, J=6.9 Hz, 2H), 2.52 (t, J=7.5 Hz, 2H), 1.61-1.12 (m, 12H), 0.88 (t, J=6.6 Hz, 3H); $^{13}$C NMR (75 MHz, CDCl$_3$) δ211.5, 144.0, 132.6, 120.7, 114.4, 111.0, 67.7, 55.9, 49.3, 45.4, 36.5, 31.8, 29.5, 29.2, 29.2, 25.5, 22.7, 14.1. MS (MALDI-TOF) m/z calculated for $C_{19}H_{30}O_4^+[M]^+$, 322.2; found, 322.2. >98% purity (as determined by RP-HPLC, method B, $t_R$=9.56 min).

Synthesis of Compound 9 (5-Hydroxy-1-(4-hydroxy-3-methoxyphenyl)tridecan-3-one, Formula 7)

Compound 9 was prepared in 32% yield as colorless oil, following the same procedure as described for the synthesis of compound 4 but with nonanal instead of butanal. $R_f$=0.15 (toluene/EtOAc=5:1, v/v).

$^1$H NMR (300 MHz, CDCl$_3$) δ6.85 (d, J=7.8 Hz, 1H), 6.69 (s, 1H), 6.68 (d, J=8.7 Hz, 1H), 5.50 (brs, 1H), 4.04 (brs, 1H), 3.89 (s, 3H), 2.91 (brs, 1H), 2.85 (t, J=6.6 Hz, 2H), 2.75 (t, J=6.6 Hz, 2H), 2.71-2.39 (m, 2H), 1.71-1.15 (m, 14H), 0.89 (s, 3H); $^{13}$C NMR (75 MHz, CDCl$_3$) δ211.5, 144.0, 132.6, 120.7, 114.4, 111.0, 67.7, 55.9, 49.3, 45.4, 36.5, 31.8, 29.5, 29.2, 29.2, 25.5, 22.7, 14.1. MS (MALDI-TOF) m/z calculated for $C_{20}H_{32}O_4^+[M]^+$, 336.2; found, 336.2. >98% purity (as determined by RP-HPLC, method B, $t_R$=13.56 min).

Synthesis of Compound 10 (5-Hydroxy-1-(4-hydroxy-3-methoxyphenyl)tetradecan-3-one, Formula 8)

Compound 10 was prepared in 32% yield as colorless oil, following the same procedure as described for the synthesis of compound 4 but with decanal instead of butanal. $R_f$=0.16 (toluene/EtOAc=5:1, v/v).

$^1$H NMR (300 MHz, CDCl$_3$) δ6.85 (d, J=7.8 Hz, 1H), 6.69 (s, 1H), 6.68 (d, J=8.7 Hz, 2H), 5.50 (brs, 1H), 4.04 (brs, 1H), 3.89 (s, 3H), 2.90 (brs, 1H), 2.85 (t, J=6.6 Hz, 2H), 2.75 (t, J=6.6 Hz, 2H), 2.56-2.34 (m, 2H), 1.49-1.18 (m, 16H), 0.98-0.79 (m, 3H); $^{13}$C NMR (75 MHz, CDCl$_3$) δ211.6, 178.4, 146.5, 144.2, 132.6, 121.5, 114.57, 111.5, 67.7, 59.3, 45.5, 36.4, 29.7, 26.1, 25.4, 24.7, 22.7, 14.1. MS (MALDI-TOF) m/z calculated for $C_{21}H_{34}O_4^+[M]^+$, 350.2; found, 350.2. >98% purity (as determined by RP-HPLC, method B, $t_R$=19.78 min).

Synthesis of Compound 14a (1-(3,4-Dimethoxyphenyl)-5-hydroxydecan-3-one, Formula 9)

To a solution of 4-(3,4-dimethoxyphenyl)butan-2-one (200 mg, 1.0 mmol) in THF (5 mL) was added LDA (2.3 mL, 2.2 mmol) at −78° C. The solution was stirred for 1 h at the same temperature. Hexanal (0.72 mL, 8.2 mmol) was added dropwise. The reaction mixture was stirred for 3 h at the same temperature, quenched with aqueous NH$_4$Cl (10 mL), and extracted with EtOAc. The organic layer was washed with water and brine, dried over MgSO$_4$, filtered, and concentrated under reduced pressure. The crude residue was purified by column chromatography on silica gel (toluene/EtOAc=10:1 to 5:1) to furnish compound 14a (97 mg, 32%) as colorless oil. $R_f$=0.26 (hexane/EtOAc=7:1, v/v).

$^1$H NMR (300 MHz, CDCl$_3$) δ6.81 (t, J=8.7 Hz, 1H), 6.69 (d, J=12.3 Hz, 2H), 4.04 (brs, 1H), 3.86 (s, 6H), 2.90-2.74 (m, 4H), 2.63-2.36 (m, 2H), 1.65-1.28 (m, 8H), 0.90 (s, 3H); $^{13}$C NMR (75 MHz, CDCl$_3$) δ211.5, 148.9, 147.4, 133.3, 120.0, 112.0, 67.7, 55.9, 49.3, 45.3, 36.4, 31.7, 29.2, 25.2, 22.6, 14.0. MS (MALDI-TOF) m/z calculated for $C_{18}H_{28}O_4^+[M+H]^+$, 309.2; found, 309.2. >98% purity (as determined by RP-HPLC, method A, $t_R$=9.86 min).

Synthesis of Compound 14b (1-(3,4-Dimethoxyphenyl)-5-hydroxydodecan-3-one, Formula 10)

Compound 14b was obtained in 32% yield as colorless oil, following the same procedure as described for the synthesis of compound 14a but with octanal instead of hexanal. $R_f$=0.26 (hexane/EtOAc=7:1, v/v).
$^1$H NMR (300 MHz, CDCl$_3$) $\delta$6.81 (t, J=8.7 Hz, 1H), 6.70 (d, J=12.3 Hz, 2H), 4.02 (brs, 1H), 3.86 (s, 6H), 2.90-2.74 (m, 4H), 2.68-2.32 (m, 2H), 1.75-1.28 (m, 10H), 0.80 (s, 3H); $^{13}$C NMR (75 MHz, CDCl$_3$) $\delta$211.5, 148.9, 147.4, 133.3, 120.0, 111.6, 111.3, 67.7, 55.9, 49.3, 45.3, 36.4, 33.8, 29.7, 25.7, 24.5, 22.6, 14.0. MS (MALDI-TOF) m/z calculated for $C_{20}H_{32}O_{4+}[M]^+$, 336.2; found, 336.2.>98% purity (as determined by RP-HPLC, method B, $t_R$=14.10 min).

Synthesis of Compound 15a (5-Hydroxy-1-phenyldecan-3-one, Formula 11)

Compound 15a was prepared in 40% yield as colorless oil, following the same procedure as described for the synthesis of compound 14a but with 4-phenylbutan-2-one instead of 4-(3,4-dimethoxyphenyl)butan-2-one. $R_f$=0.43 (hexane/EtOAc=5:1, v/v).
$^1$H NMR (300 MHz, CDCl$_3$) $\delta$7.30 (t, J=7.5 Hz, 2H), 7.21 (d, J=7.2 Hz, 3H), 4.05 (brs, 1H), 2.99 (brs, 1H), 2.93 (t, J=7.5 Hz, 2H), 2.77 (t, J=7.5 Hz, 2H), 2.62-2.46 (m, 2H), 1.49-1.30 (m, 8H), 0.95-0.82 (m, 3H); $^{13}$C NMR (75 MHz, CDCl$_3$) $\delta$211.3, 140.7, 128.6, 128.3, 126.2, 67.6, 49.3, 45.1, 36.4, 31.7, 29.5, 25.2, 22.6, 14.1. MS (MALDI-TOF) m/z calculated for $C_{16}H_{24}O_2^+[M+H]^+$, 249.2; found, 249.9.>98% purity (determined by RP-HPLC, method A, $t_R$=16.57 min).

Synthesis of Compound 15b (5-Hydroxy-1-phenyldodecan-3-one, Formula 12)

Compound 15b was prepared in 38% yield as colorless oil, following the same procedure as described for the synthesis of compound 15a but with octanal instead of hexanal. $R_f$=0.43 (hexane/EtOAc=5:1, v/v).
$^1$H NMR (300 MHz, CDCl$_3$) $\delta$7.31 (t, J=7.5 Hz, 2H), 7.20 (d, J=7.2 Hz, 3H), 4.04 (brs, 1H), 2.98 (brs, 1H), 2.93 (t, J=7.5 Hz, 2H), 2.79 (t, J=7.5 Hz, 2H), 2.57-2.46 (m, 2H), 1.60-1.28 (m, 10H), 0.96-0.83 (m, 3H); $^{13}$C NMR (75 MHz, CDCl$_3$) $\delta$211.0, 152.6, 149.4, 147.3, 137.1, 120.3, 115.9, 67.7, 56.2, 49.4, 45.1, 36.5, 31.8, 29.5, 29.2, 25.5, 22.7, 14.1. MS (MALDI-TOF) m/z calculated for $C_{18}H_{28}O_2^+[M+Na]^+$, 299.2; found, 299.1.>98% purity (as determined by RP-HPLC, method B, $t_R$=23.28 min).

Synthesis of Compound 16a (1-(4-Fluoro-3-methoxyphenyl)-5-hydroxydecan-3-one, Formula 13)

Compound 16a was prepared in 33% yield as colorless oil, following the same procedure as described for the synthesis of compound 14a but with 4-(4-fluoro-3-methoxyphenyl)butan-2-one instead of 4-(3,4-dimethoxyphenyl)butan-2-one. $R_f$=0.32 (hexane/EtOAc=5:1, v/v).
$^1$H NMR (300 MHz, CDCl$_3$) ($\delta$6.99 (t, J=9.8 Hz, 1H), 6.79 (d, J=8.1 Hz, 1H), 6.71 (brs, 1H), 4.05 (s, 1H), 3.89 (s, 3H), 2.94-2.84 (m, 3H), 2.77 (t, J=7.3 Hz, 2H), 2.57-2.46 (m, 2H), 1.49-1.30 (m, 8H), 0.98-0.81 (m, 3H); $^{13}$C NMR (75 MHz, CDCl$_3$) 211.0, 152.6, 149.4, 147.5, 137.1, 120.3, 116.1, 113.6., 67.7, 56.2, 49.4, 45.1, 36.4, 34.5, 32.8, 31.7, 29.1, 25.1, 22.6, 14.1. MS (MALDI-TOF) m/z calculated for $C_{17}H_{25}FO_3[MH]$, 295.2; found, 295.0.>98% purity (as determined by RP-HPLC, method A, $t_R$=15.63 min).

Synthesis of Compound 16b (1-(4-Fluoro-3-methoxyphenyl)-5-hydroxydodecan-3-one, Formula 14)

Compound 16b was prepared in 38% yield as colorless oil, following the same procedure as described for the synthesis of compound 16a but with octanal instead of hexanal. $R_f$=0.32 (hexane/EtOAc=5:1, v/v).
$^1$H NMR (300 MHz, CDCl$_3$) ($\delta$6.99 (t, J=9.8 Hz, 1H), 6.80 (d, J=8.1 Hz, 1H), 6.70 (brs, 1H), 4.04 (s, 1H), 3.88 (s, 3H), 3.02-2.81 (m, 3H), 2.76 (t, J=6.9 Hz, 2H), 2.57-2.49 (m, 2H), 1.48-1.28 (m, 10H), 0.97-0.80 (m, 3H); $^{13}$C NMR (75 MHz, CDCl$_3$) $\delta$211.0, 152.6, 149.4, 147.5, 137.1, 120.9, 116.1, 114.0, 67.7, 56.2, 49.4, 45.1, 36.4, 34.5, 32.8, 31.7, 29.1, 26.1, 25.1, 22.6, 14.0. MS (MALDI-TOF) m/z calculated for $C_{19}H29FO_3^+[M+H]^+$, 325.2; found, 325.3.>98% purity (as determined by RP-HPLC, method B, $t_R$=21.19 min).

Synthesis of Compound 17a (1-(4-Fluorophenyl)-5-hydroxydecan-3-one, Formula 15)

Compound 17a was prepared in 40% yield as colorless oil, following the same procedure as described for the synthesis of compound 14a but with 4-(4-fluorophenyl)butan-2-one instead of 4-(3,4-dimethoxyphenyl)butan-2-one. $R_f$=0.29 (hexane/EtOAc=5:1, v/v).
$^1$H NMR (300 MHz, CDCl$_3$) ($\delta$7.22-7.13 (m, 2H), 6.97 (d, J=8.7 Hz, 1H), 6.96 (d, J=8.4 Hz, 1H), 4.03 (s, 1H), 2.99 (s, 1H), 2.88 (t, J=6.6 Hz, 2H), 2.75 (t, J=6.6 Hz, 2H), 2.68-2.39 (m, 2H), 1.64-1.40 (m, 8H), 0.90 (s, 3H); $^{13}$C NMR (75 MHz, CDCl$_3$) $\delta$211.0, 148.6, 147.4, 132.5, 115.1, 112.9, 116.1, 67.7, 63.2, 49.4, 45.1, 36.4, 34.8, 32.2, 31.0, 29.3, 26.1, 25.4, 22.7, 14.0. MS (MALDI-TOF) m/z calculated for $C_{16}H23FO_2[MH]$, 265.4; found, 264.9.>98% purity (as determined by RP-HPLC, method A, $t_R$=17.31 min).

Synthesis of Compound 17b (1-(4-Fluorophenyl)-5-hydroxydodecan-3-one, Formula 16)

Compound 17b was prepared in 45% yield as colorless oil, following the same procedure as described for the synthesis of compound 17a but with by using octanal instead of hexanal. $R_f$=0.29 (hexane/EtOAc=5:1, v/v).
$^1$H NMR (300 MHz, CDCl$_3$) ($\delta$7.18-7.08 (m, 2H), 6.97 (d, J=8.4 Hz, 1H), 6.94 (d, J=8.7 Hz, 1H), 4.03 (brs, 1H), 3.00 (s, 1H), 2.88 (t, J=6.6 Hz, 2H), 2.75 (t, J=6.6 Hz, 2H), 2.68-2.39 (m, 2H), 1.63-1.28 (m, 10H), 0.88 (s, 3H); $^{13}$C NMR (75 MHz, CDCl$_3$) 211.5, 145.7, 144.1, 132.5, 120.6, 114.4, 114.3, 111.8, 67.7, 64.4, 49.3, 45.5, 36.4, 31.8, 29.8, 29.3, 25.5, 22.7, 14.9, 14.1. MS (MALDI-TOF) m/z calculated for $C_{18}H_{27}FO_2^+[M]^+$, 294.2; found, 294.0.>98% purity (as determined by RP-HPLC, method B, $t_R$=23.81 min).

Synthesis of Compound 18a (5-Hydroxy-1-(4-hydroxyphenyl)decan-3-one, Formula 17)

Compound 18a was prepared in 40% yield as colorless oil, following the same procedure as described for the synthesis of compound 14a but with 4-(4-hydroxyphenyl)butan-2-one instead of 4-(3,4-dimethoxyphenyl)butan-2-one. $R_f$=0.23 (hexane/EtOAc=5:1, v/v).

$^1$H NMR (300 MHz, CDCl$_3$) δ7.04 (d, J=7.2 Hz, 2H), 6.75 (d, J=7.2 Hz, 2H), 5.77 (brs, 1H), 4.05 (s, 1H), 3.19 (brs, 1H), 2.84 (t, J=6.6 Hz, 2H), 2.74 (t, J=6.6 Hz, 2H), 2.68-2.41 (m, 2H), 1.69-1.12 (m, 8H), 0.89 (s, 3H); $^{13}$C NMR (75 MHz, CDCl$_3$) 211.2, 159.7, 142.4, 129.5, 120.6, 114.1, 111.5, 67.7, 55.1, 49.3, 45.0, 36.5, 31.7, 29.6, 25.1, 22.6, 22.2, 14.0. MS (MALDI-TOF) m/z calculated for $C_{16}H_{24}O_3^+$[M+H]$^+$, 265.2; found, 265.9.>98% purity (as determined by RP-HPLC, method A, $t_R$=6.60 min).

Synthesis of Compound 18b
(5-Hydroxy-1-(4-hydroxyphenyl)dodecan-3-one, Formula 18)

Compound 18b was prepared in 25% yield as colorless oil, following the same procedure as described for the synthesis of compound 18a but with octanal instead of hexanal. $R_f$=0.23 (hexane/EtOAc=5:1, v/v).

$^1$H NMR (300 MHz, CDCl$_3$) (δ7.05 (d, J=8.1 Hz, 2H), 6.76 (d, J=8.1 Hz, 2H), 5.09 (brs, 1H), 4.04 (s, 1H), 3.15 (brs, 1H), 2.85 (t, J=6.6 Hz, 2H), 2.74 (t, J=6.6 Hz, 2H), 2.68-2.45 (m, 2H), 1.58-1.15 (m, 10H), 0.89 (s, 3H); $^{13}$C NMR (75 MHz, CDCl$_3$) 211.2, 159.7, 142.4, 129.7, 129.5, 129.4, 120.6, 114.1, 111.5, 67.7, 55.2, 49.4, 45.0, 36.4, 31.8, 29.5, 29.2, 25.5, 22.6, 14.1. MS (MALDI-TOF) m/z calculated for $C_{18}H_{28}O_3^+$[M+H]$^+$, 293.2; found, 293.1.>98% purity (as determined by RP-HPLC, method B, $t_R$=9.05 min).

Synthesis of Compound 19a (1-(3-Ethoxy-4-hydroxyphenyl)-5-hydroxydecan-3-one, Formula 19)

Compound 19a was prepared in 35% yield as colorless oil, following the same procedure as described for the synthesis of compound 14a but with 4-(3-ethoxy-4-hydroxyphenyl)butan-2-one instead of 4-(3,4-dimethoxyphenyl)butan-2-one. $R_f$=0.32 (hexane/EtOAc=4:1, v/v).

$^1$H NMR (300 MHz, CDCl$_3$) δ6.84 (d, J=7.8 Hz, 1H), 6.65 (s, 1H), 6.82-6.61 (m, 1H), 5.59 (brs, 1H), 4.10 (q, J=7.2 Hz, 2H), 2.84 (t, J=6.6 Hz, 2H), 2.76 (t, J=6.6 Hz, 2H), 2.67-2.45 (m, 2H), 1.45 (t, J=7.2 Hz, 3H), 1.58-1.15 (m, 8H), 0.90 (s, 3H); $^{13}$C NMR (75 MHz, CDCl$_3$) δ200.8, 148.1, 146.8, 142.6, 127.1, 124.2, 123.4, 114.8, 109.3, 56.0, 45.7, 40.7, 31.9, 29.5, 29.3, 29.3, 24.6, 22.7, 14.1. MS (MALDI-TOF) m/z calculated for $C_{16}H_{24}O_3^{30}$ [M+]$^+$, 265.4; found, 265.9.>98% purity (as determined by RP-HPLC, method A, $t_R$=9.25 min).

Synthesis of Compound 19b (1-(3-Ethoxy-4-hydroxyphenyl)-5-hydroxydodecan-3-one, Formula 20)

Compound 19b was prepared in 27% yield as colorless oil, following the same procedure as described for the synthesis of compound 19a but with octanal instead of hexanal. $R_f$=0.32 (hexane/EtOAc=4:1, v/v).

$^1$H NMR (300 MHz, CDCl$_3$) δ6.85 (d, J=7.8 Hz, 1H), 6.68 (s, 1H), 6.66 (d, J=7.2 Hz, 1H), 5.56 (brs, 1H), 4.10 (q, J=7.2 Hz, 2H), 2.84 (t, J=6.6 Hz, 2H), 2.74 (t, J=6.6 Hz, 2H), 2.91-2.45 (m, 2H), 1.46 (t, J=6.9 Hz, 3H), 1.84-1.19 (m, 10H), 0.90 (s, 3H); $^{13}$C NMR (75 MHz, CDCl$_3$) δ211.1, 159.7, 142.4, 129.7, 129.5, 129.4, 120.6, 114.0, 111.5 67.7, 55.2, 49.4, 45.0, 36.4, 31.8, 29.8, 29.5, 29.2, 25.5, 22.6, 14.0; MS (MALDI-TOF) m/z calculated for $C_{18}H_{28}O_3^+$[M+H]$^+$, 293.2; found, 293.1.>98% purity (as determined by RP-HPLC, method B, $t_R$=12.91 min).

Synthesis of Compound 20a
(5-Hydroxy-1-(3-methoxyphenyl)decan-3-one, Formula 21)

Compound 20a was prepared in 32% yield as colorless oil, following the same procedure as described for the synthesis of compound 14a but with 4-(3-methoxyphenyl)butan-2-one instead of 4-(3,4-dimethoxyphenyl)-butan-2-one. $R_f$=0.34 (hexane/EtOAc=5:1, v/v).

$^1$H NMR (300 MHz, CDCl$_3$) (δ7.22 (t, J=7.8 Hz, 1H), 6.79-6.72 (m, 3H), 4.04 (brs, 1H), 3.81 (s, 3H), 2.96 (s, 1H), 2.90 (t, J=7.2 Hz, 2H), 2.78 (t, J=7.2 Hz, 2H), 2.61-2.49 (m, 2H), 1.68-1.21 (m, 8H), 0.90 (s, 3H); $^{13}$C NMR (75 MHz, CDCl$_3$) (δ211.2, 159.7, 142.4, 129.5, 120.6, 114.1, 111.5, 67.7, 55.1, 49.3, 45.0, 36.5, 31.7, 29.6, 25.1, 22.6, 14.0. MS (MALDI-TOF) m/z calculated for $C_{17}H_{26}O_3^{+1}$[M]$^+$, 278.2; found, 278.0. >98% purity (as determined by RP-HPLC, method A, $t_R$=15.50 min).

Synthesis of Compound 20b
(5-Hydroxy-1-(3-methoxyphenyl)dodecan-3-one, Formula 22)

Compound 20b was prepared in 34% yield as colorless oil, following the same procedure as described for the synthesis of compound 20a but with octanal instead of hexanal. $R_f$=0.34 (hexane/EtOAc=5:1, v/v).

$^1$H NMR (300 MHz, CDCl$_3$) (δ7.22 (t, J=7.8 Hz, 1H), 6.79-6.73 (m, 3H), 4.04 (brs, 1H), 3.81 (s, 3H), 2.95-2.86 (m, 3H), 2.82-2.74 (m, 2H), 2.52 (t, J=9.0 Hz, 2H), 1.61-1.18 (m, 10H), 0.88 (s, 3H); $^{13}$C NMR (75 MHz, CDCl$_3$) (δ211.2, 159.7, 142.4, 129.7, 120.6, 114.1, 111.5, 67.7, 55.2, 49.3, 45.0, 36.5, 31.8, 29.6, 29.2 25.5, 22.7, 14.1. MS (MALDI-TOF) m/z calculated for $C_{19}H_{30}O_3^+$[M+H]$^+$, 307.2; found, 307.2.>98% purity (as determined by RP-HPLC, method B, $t_R$=21.69 min).

Synthesis of Compound 21a ((E)-5-Hydroxy-1-(4-hydroxy-3-methoxyphenyl)dec-1-en-3-one, Formula 23)

To a solution of compound 12 (150 mg, 0.7 mmol) in THF (5 mL) was added LDA (1.7 mL, 1 M in THF/hexanes) at −78° C. under Ar. The solution was stirred for 1 h at the same temperature. Hexanal (0.52 mL, 6.2 mmol) was slowly added. The reaction mixture was stirred for 3 h at the same temperature. The reaction mixture was quenched with aqueous NH$_4$Cl (10 mL) and extracted with EtOAc. The organic layer was washed with water and brine, dried over MgSO$_4$, filtered, and concentrated under reduced pressure. The crude residue was purified by column chromatography on silica gel (eluting with a mixture of hexane/EtOAc, 10:1 to 3:1, v/v) to furnish compound 21a (70 mg, 31%). $R_f$=0.25 (hexane/EtOAc=5:1, v/v).

$^1$H NMR (300 MHz, CDCl$_3$) (δ7.53 (d, J=16.2 Hz, 1H), 7.12 (d, J=8.1 Hz, 1H), 7.07 (s, 1H), 6.95 (d, J=8.1 Hz, 1H), 6.61 (d, J=16.2 Hz, 1H), 4.15 (brs, 1H), 3.95 (s, 3H), 2.93-2.71 (m, 1H), 2.39 (s, 1H), 1.82-1.25 (m, 8H), 0.92 (s, 3H); $^{13}$C NMR (75 MHz, CDCl$_3$) δ201.0, 148.6, 146.9, 143.9, 126.7, 124.1 123.8, 114.9, 109.5, 68.1, 56.0, 46.5, 36.5, 31.8, 25.2, 22.6, 14.1. MS (MALDI-TOF) m/z calculated for $C_{17}H_{24}O_4^+$[M+H]$^+$, 293.2; found, 293.1.>98% purity (as determined by RP-HPLC, method A, $t_R$=6.91 min).

Synthesis of Compound 21b ((E)-5-Hydroxy-1-(4-hydroxy-3-methoxyphenyl)dodec-1-en-3-one, Formula 24)

Compound 21b was prepared in 31% yield, following the same procedure as described for the synthesis of compound 21a but with octanal instead of hexanal. $R_f$=0.25 (hexane/EtOAc=5:1, v/v).

$^1$H NMR (300 MHz, CDCl$_3$) (δ7.53 (d, J=16.2 Hz, 1H), 7.11 (d, J=8.1 Hz, 1H), 7.08 (s, 1H), 6.94 (d, J=8.1 Hz, 1H), 6.60 (d, J=16.2 Hz, 1H), 4.15 (brs, 1H), 3.91 (s, 3H), 2.93-2.68 (m, 1H), 2.35 (s, 1H), 2.75-1.21 (m, 10H), 0.89 (s, 3H); $^{13}$C NMR (75 MHz, CDCl$_3$) δ200.1, 148.5, 146.9, 143.8, 126.7, 124.1, 123.7, 114.9, 109.5, 68.0, 56.0, 46.5, 36.6, 31.8, 29.6, 29.2, 25.5, 22.6, 14.0. MS (MALDI-TOF) m/z calculated for C$_{19}$H$_{28}$O$_3$$^+$[M+Na]$^+$, 343.4; found, 343.2.>98% purity (as determined by RP-HPLC, method B, $t_R$ =11.97 min).

Synthesis of Compound 22a ((E)-1-(4-Fluoro-3-methoxyphenyl)-5-hydroxydec-1-en-3-one, Formula 25)

Compound 22a was prepared in 40% yield, following the same procedure as described for the synthesis of compound 21a but with (E)-4-(4-fluoro-3-methoxyphenyl)but-3-en-2-one instead of compound 12. $R_f$=0.32 (hexane/EtOAc=5:1, v/v).

$^1$H NMR (300 MHz, CDCl$_3$) (δ7.53 (d, J=16.2 Hz, 1H), 7.15 (d, J=8.1 Hz, 2H), 7.11 (s, 1H), 6.66 (d, J=16.2 Hz, 1H), 4.16 (brs, 1H), 3.95 (s, 3H), 3.2 (s, 1H), 2.93-2.72 (m, 2H), 1.63-1.33 (m, 8H), 0.89 (s, 3H); $^{13}$C NMR (75 MHz, CDCl$_3$) δ200.1, 155.7, 152.3, 148.2, 148.0, 142.6, 130.9, 126.2, 122.2, 116.5, 112.3, 67.9, 58.0, 46.9, 36.6, 31.8, 25.6, 25.3, 22.7, 22.6, 14.0. MS (MALDI-TOF) m/z calculated for C$_{17}$H$_{25}$FO$_3$$^+$[M]$^+$, 294.2; found, 294.0.>98% purity (as determined by RP-HPLC, method A, $t_R$ =16.32 min).

Synthesis of Compound 22b ((E)-1-(4-Fluoro-3-methoxyphenyl)-5-hydroxydodec-1-en-3-one, Formula 26)

Compound 22b was prepared in 31% yield, following the same procedure as described for the synthesis of compound 22a but with octanal instead of hexanal. $R_f$=0.32 (hexane/EtOAc=5:1, v/v).

$^1$H NMR (300 MHz, CDCl$_3$) δ7.55 (d, J=16.2 Hz, 1H), 7.27 (s, 1H), 7.12 (d, J=8.1 Hz, 2H), 6.66 (d, J=16.2 Hz, 1H), 4.15 (brs, 1H), 3.95 (s, 3H), 3.2 (s, 1H), 2.93-2.79 (m, 2H), 1.60-1.30 (m, 10H), 0.89 (s, 3H); $^{13}$C NMR (75 MHz, CDCl$_3$) δ200.1, 155.7, 152.3, 148.2, 148.0, 142.6, 130.9, 126.2, 122.2, 116.5, 112.3, 67.9, 58.0, 46.9, 36.6, 31.8, 29.5, 29.3 25.6, 25.3, 22.7, 22.6, 14.0. MS (MALDI-TOF) m/z calculated for C$_{19}$H$_{27}$FO$_3$$^+$[M]$^+$,323.2; found, 323.2.>98% purity (as determined by RP-HPLC, method B, $t_R$ =22.13 min).

Synthesis of Compound 23a ((E)-1-(4-Hydroxy-3-methoxyphenyl)dec-1-en-3-one)

To a solution of 4-hydroxy-3-methoxybenzaldehyde (913 mg, 6.0 mmol) in MeOH (10 mL) was added (L)-proline (86 mg, 0.75 mmol) and nonan-2-one (0.87 mL, 5.0 mmol) at 25° C. under Ar. After 30 min, triethylamine (0.21 mL, 1.5 mmol) was introduced. The reaction mixture was stirred 25° C. for 48 h and then quenched with water and extracted with EtOAc. The combined organic layer was dried over MgSO$_4$, filtered, and concentrated under reduced pressure. The crude residue was purified by column chromatography on silica gel (hexane/EtOAc=10:1 to 3:1, v/v) to furnish compound 23a (746 mg, 45%) as a white solid. $R_f$=0.32 (hexane/EtOAc=5:1, v/v).

$^1$H NMR (300 MHz, CDCl$_3$) δ7.51 (d, J=16.2 Hz, 1H), 7.12 (d, J=7.8 Hz, 1H), 7.08 (s, 1H), 6.94 (d, J=8.1 Hz, 1H), 6.63 (d, J=16.2 Hz, 1H), 5.94 (s, 1H), 3.95 (s, 3H), 2.66 (t, J=7.2 Hz, 2H), 1.78-1.56 (m, 2H), 1.54-1.19 (m, 8H), 0.88 (s, 3H); $^{13}$C NMR (75 MHz, CDCl$_3$) δ201.0, 148.4, 147.0, 142.8, 126.9, 123.9, 123.3, 114.9, 109.6, 55.9, 40.6, 31.7, 29.3, 29.1, 24.6, 22.6, 14.0. MS (MALDI-TOF) m/z calculated for C$_{14}$H$_{24}$O$_3$$^+$[M]$^+$,276.2; found, 276.2.>98% purity (as determined by RP-HPLC, method A, $t_R$=24.61 min).

Synthesis of Compound 23b ((E)-1-(4-Hydroxy-3-methoxyphenyl)dodec-1-en-3-one Compound 23b was prepared in 60% yield as a white solid, following the same procedure as described for the synthesis of compound 23a but with octanal instead of hexanal. $R_f$=0.32 (hexane/EtOAc=5:1, v/v).

$^1$H NMR (300 MHz, CDCl$_3$) (δ7.51 (d, J=16.2 Hz, 1H), 7.12 (d, J=7.8 Hz, 1H), 7.08 (s, 1H), 6.94 (d, J=8.1 Hz, 1H), 6.63 (d, J=16.2 Hz, 1H), 5.92 (s, 1H), 3.95 (s, 3H), 2.66 (t, J=7.2 Hz, 2H), 1.78-1.56 (m, 2H), 1.51-1.13 (m, 12H), 0.88 (s, 3H); $^{13}$C NMR (75 MHz, CDCl$_3$) δ200.1, 148.1, 146.8, 142.6, 127.1, 124.2, 123.4, 114.8, 109.3, 55.9, 45.7, 40.7, 31.9, 29.5, 29.3, 29.2, 24.6, 22.7 14.1. MS (MALDI-TOF) m/z calculated for C$_{19}$H$_{28}$O$_3$$^+$[M]$^+$, 304.2; found, 304.2.>98% purity (as determined by RP-HPLC, method C, $t_R$ =10.56 min).

Synthesis of Compound 24a (1-(4-Hydroxy-3-methoxyphenyl)decan-3-one)

To a solution of compound 23a (100 mg, 0.36 mmol) in MeOH (10 mL) was added 10% Pd/C (1.9 mg, 0.02 mmol). The reaction mixture was purged with H$_2$ gas and stirred for 2 h and then was filtered through a Celite pad and concentrated under reduced pressure. The crude residue was purified by column chromatography on silica gel (hexane/EtOAc=12:1, v/v) to furnish compound 24a (76 mg, 75%) as a white solid. $R_f$=0.31 (hexane/EtOAc=7:1, v/v).

$^1$H NMR (300 MHz, CDCl$_3$) (δ6.84 (d, J=7.8 Hz, 1H), 6.70 (s, 1H), 6.69 (d, J=10.2 Hz, 1H), 5.51 (s, 1H), 3.91 (s, 3H), 2.84 (t, J=6.6 Hz, 2H), 2.79 (t, J=6.6 Hz, 2H), 2.39 (t, J=7.2 Hz, 2H), 1.71-1.52 (m, 2H), 1.49-1.21 (m, 8H), 0.89 (s, 3H); $^{13}$C NMR (75 MHz, CDCl$_3$) δ210.7, 146.6, 143.9, 132.9, 120.7, 114.5, 111.2, 55.8, 44.5, 42.9, 31.6, 29.5, 29.1, 29.0, 23.8, 22.6, 14.0. MS (MALDI-TOF) m/z calculated for C$_{17}$H$_{26}$O$_3$$^+$[M]$^+$, 278.2; found, 278.2.>98% purity (as determined by RP-HPLC, method A, $t_R$ =24.76 min).

Synthesis of compound 24b (1-(4-Hydroxy-3-methoxyphenyl)dodecan-3-one)

Compound 24b was prepared in 97% yield as a white solid, by following the same procedure as described for the synthesis of compound 24a but with compound 23b instead of compound 23a. $R_f$=0.33 (hexane/EtOAc=7:1, v/v).

$^1$H NMR (300 MHz, CDCl$_3$) (δ6.84 (d, J=7.8 Hz, 1H), 6.70 (s, 1H), 6.69 (d, J=10.2 Hz, 1H), 5.49 (s, 1H), 3.89 (s, 3H), 3.21 (s, 1H), 2.84 (t, J=6.6 Hz, 2H), 2.74 (t, J=6.6 Hz, 2H), 2.39 (t, J=7.2 Hz, 2H), 1.58-1.52 (m, 2H), 1.31-1.21 (m, 10H), 0.89 (s, 3H); $^{13}$C NMR (75 MHz, CDCl$_3$) δ210.7, 146.3, 143.8, 133.1, 120.8, 114.3, 111.0, 55.9, 44.6, 43.2, 31.9, 29.5, 29.4, 29.2, 29.2, 23.8, 22.7, 14.1. MS (MALDI-TOF) m/z calculated for $C_{19}H_{30}O_3+[M]^+$,306.2; found, 306.2.>98% purity (as determined by RP-HPLC, method C, $t_R$=10.51 min).

Synthesis of Compound 25 ((R)-4-Hydroxyundecan-2-one)

To a suspension of (D)-proline (0.23 g, 2.0 mmol) in acetone (100 mL) was added 1-octanal (3.1 mL, 20 mmol) in one portion at 25° C. The reaction mixture was stirred for 48 h and then was quenched with brine (50 mL) and extracted with EtOAc (3×50 mL). The combined organic layer was dried over $MgSO_4$ and concentrated under reduced pressure. The crude residue was purified by column chromatography on silica gel (hexane/EtOAc=7:1 to 3:1, v/v) to furnish compound 25 as colorless oil (1.8 g, 48%). $R_f$=0.23 (hexane/EtOAc=5:1, v/v).

$^1$H NMR (300 MHz, $CDCl_3$) (δ4.05 (s, 1H), 2.96 (s, 1H), 2.68-2.50 (m, 2H), 2.19 (s, 3H), 1.51-1.29 (m, 12H), 0.90 (s, 3H).

Synthesis of Compound 26 ((R)-4-((tert-Butyldimethylsilyl)oxy)undecan-2-one)

To a solution of compound 25 (900 mg, 5.69 mmol) in $CH_2Cl_2$ (50 mL) were added imidazole (1.16 g, 17.1 mmol) and TBDMSCl (1.29 g, 8.5 mmol). The reaction mixture was stirred for 10 h at room temperature and then was quenched with water and extracted with diethyl ether. The organic layer was dried over $MgSO_4$, filtered, and concentrated under reduced pressure. The crude residue was purified by column chromatography on silica gel (hexane/EtOAc=15:1 to 7:1, v/v) to furnish compound 26 (1.35 g, 87%) as a white solid. $R_f$=0.75 (hexane/EtOAc=8:1, v/v).

$^1$H NMR (300 MHz, $CDCl_3$) δ4.15 (t, J=6.3 Hz, 1H), 2.67-2.18 (m, 2H), 2.18 (s, 3H), 1.44 (brs, 2H), 1.32-1.22 (m, 10H), 0.97-0.76 (m, 12H), 0.07 (s, 3H), 0.04 (s, 3H).

Synthesis of Compound 27 ((R)-6-Heptyl-2,2,8,8,9,9-hexamethyl-4-methylene-3,7-dioxa-2,8-disiladecane)

To a solution of compound 26 (272 mg, 1.0 mmol) in $CH_2Cl_2$ were added DIPEA (388 mg, 3.0 mmol) and TMSOTf (0.271 mL, 1.5 mmol) at 0° C. The reaction mixture was stirred at 0° C. for 3 h and then was quenched with saturated aqueous $NaHCO_3$ (20 mL) and extracted with $CH_2Cl_2$. The organic layer was washed with water and brine, dried over $MgSO_4$, and concentrated under reduced pressure. The residue was dissolved in diethyl ether (20 mL) and washed with water and brine, and dried over $MgSO_4$, filtered, and concentrated under reduced pressure to provide compound 27 which was used in the next step without further purification. $R_f$=0.89 (hexane/EtOAc=8:1, v/v).

Synthesis of Compound 28 ((R,E)-5-Hydroxy-1-(4-hydroxy-3-methoxyphenyl)dodec-1-en-3-one, Formula 27)

To a solution of compound 27 and vanillin (152 mg, 1.0 mmol) in $CH_2Cl_2$ (10 mL) was added $BF_3.OEt_2$ (0.19 mL, 1.5 mmol) for 10 min at 0° C. The reaction mixture was stirred at 0° C. for additional 30 min, followed by the addition of triethylamine (0.84 mL, 6.0 mmol) in one portion. The reaction mixture was stirred for 20 min at the same temperature and then was quenched with saturated aqueous $NaHCO_3$ (10 mL) and extracted with $CH_2Cl_2$. The organic layer was washed with water and brine, dried over $MgSO_4$, filtered, and concentrated under reduced pressure. The crude residue was purified by column chromatography on silica gel (hexane/EtOAc=5:1 to 2:1, v/v) to furnish compound 28 (82 mg, 30% over 2 steps) as a yellow solid. $R_f$=0.29 (hexane/EtOAc=5:1, v/v).

$^1$H NMR (300 MHz, $CDCl_3$) δ7.52 (d, J=16.5 Hz, 1H), 7.09 (t, J=8.1 Hz, 2H), 6.94 (d, J=8.1 Hz, 1H), 6.60 (d, J=16.5 Hz, 1H), 4.15 (brs, 1H), 3.94 (s, 3H), 3.41 (s, 1H), 2.91-2.71 (m, 2H), 1.61-1.24 (m, 12H), 0.88 (s, 3H); $^{13}$C NMR (75 MHz, $CDCl_3$) δ201.0, 148.6, 146.9, 143.8, 126.7, 124.2, 123.7, 114.9, 109.5, 68.0, 56.0, 46.5, 36.6, 31.8, 29.6, 29.3, 25.6, 22.7, 14.1.

Synthesis of Compound 29 ((R)-5-Hydroxy-1-(4-hydroxy-3-methoxyphenyl)dodecan-3-one, Formula 28)

To a solution of compound 28 (60 mg, 0.19 mmol) in MeOH (10 mL) was added 10% Pd/C. The reaction mixture was purged with $H_2$ gas and stirred for 2 h. The reaction mixture was filtered through a Celite pad and concentrated under reduced pressure. The crude residue was purified by column chromatography on silica gel (hexane/EtOAc=3:1, v/v) to prepare compound 29 (57 mg, 0.18 mmol) as colorless oil. $R_f$=0.32 (hexane/EtOAc=5:1, v/v).

$^1$H NMR (300 MHz, $CDCl_3$) δ6.82 (d, J=7.8 Hz, 1H), 6.66 (s, 1H), 6.65 (d, J=9.0 Hz, 2H), 5.52 (s, 1H), 4.02 (brs, 1H), 3.87 (s, 3H), 2.95 (s, 1H), 2.85-2.70 (m, 4H), 2.55-2.49 (m, 2H), 1.47-1.26 (m, 12H), 0.86 (d, J=6.5 Hz, 3H); $^{13}$C NMR (75 MHz, $CDCl_3$) δ201.0, 148.3, 147.0, 142.8, 127.0, 123.9, 123.4, 115.0, 109.6, 55.9, 40.6, 31.7, 29.3, 29.1, 24.6, 22.6, 14.1.>98% purity (as determined by RP-HPLC, method B, $t_R$=9.53 min).

Synthesis of Compound 31 ([(But-3-en-1-yloxy)methyl]benzene)

To a suspension of sodium hydride (1.9 g, 48 mmol) in dry THF (60 mL) was added 3-buten-1-ol (2.3 mL, 27.0 mmol) dropwise at 0° C. The solution was stirred 1 h at the same temperature. Benzyl bromide (3.5 mL, 29.1 mmol) was added dropwise to the solution. The reaction mixture was stirred for 16 h and quenched with brine (50 mL), followed by the extraction with diethyl ether (3×50 mL). The combined organic layer was dried over $MgSO_4$ and concentrated under reduced pressure to give compound 31 as colorless oil (3.9 g, 90%). $R_f$=0.89 (hexane/EtOAc=8:1, v/v).

$^1$H NMR (300 MHz, $CDCl_3$) δ7.49-7.23 (m, 5H), 5.91-5.82 (m, 1H), 5.10 (t, J=15.2 Hz, 2H), 4.55 (s, 3H), 3.55 (t, J=6.7 Hz, 2H), 2.41 (q, J=6.7 Hz, 2H).

Synthesis of Compound 32 (2-[2-(Benzyloxy)ethyl]oxirane)

To a solution of compound 32 (3.0 g, 19.0 mmol) in dry $CH_2Cl_2$ (100 mL) was added $NaHCO_3$ (2.1 g, 25.0 mmol) at 0° C., followed by the addition of m-CPBA (70-75% w/w, 8.3 g, 38.0 mmol). The reaction mixture was stirred for 16 h and then was filtered through a Celite pad and concentrated under reduced pressure. The crude residue was dissolved in water (50 mL) and extracted with diethyl ether (3×50 mL). The combined organic layer was washed with 3 N NaOH (3×50 mL), brine (50 mL), dried over $MgSO_4$, and concentrated. The crude residue was purified by column chromatography on silica gel (hexane/EtOAc=4:1) to furnish compound 32 (racemate) as colorless oil (1.56 g, 66% over 2 steps). $R_f$=0.51 (hexane/EtOAc=7:1, v/v).
$^1$H NMR (300 MHz, CDCl$_3$) δ7.49-7.23 (m, 5H), 4.56 (s, 2H), 3.65 (q, J=5.6 Hz, 2H), 3.10 (brs, 1H), 2.78 (brs, 1H), 2.55 (brs, 1H), 1.97-1.76 (m, 2H).

Synthesis of Compound 33 ((S)-2-[2-(Benzyloxy)ethyl]oxirane)

To a solution of (±)-compound 32 (3.1 g, 17.0 mmol) in THF (1 mL) were added (S,S)-(+)-N,N'-bis (3,5-di-tert-butylsalicyclidene)-1,2-cyclohexanediaminocobalt(II) (0.21 g, 0.4 mmol) and AcOH (80 μL, 1.4 mmol). The reaction mixture was cooled to 0° C., and H$_2$O (0.17 mL, 9.5 mmol) was added in one portion. The reaction mixture was allowed to warm to room temperature and stirred for 16 h. The reaction mixture was quenched with H$_2$O and extracted with EtOAc. The combined organic layer was washed with water (50 mL) and brine (50 mL), dried over MgSO$_4$, filtered, and concentrated under reduced pressure. The crude residue was purified by column chromatography on silica gel (hexane/EtOAc=12:1 to 3:1) to furnish compound 33 (1.5 g, 50%) as a pale yellow oil. $R_f$=0.51 (hexane/EtOAc=7:1, v/v).
$^1$H NMR (300 MHz, CDCl$_3$) δ7.43-7.23 (m, 5H), 4.56 (s, 2H), 3.65 (q, J=5.6 Hz, 2H), 3.10 (brs, 1H), 2.78 (brs, 1H), 2.55 (brs, 1H), 1.97-1.76 (m, 2H).

Synthesis of Compound 34 ((R)-1-(Benzyloxy)dec-5-yn-3-ol)

To a solution of 1-hexyne (349 mg, 4.3 mmol) in dry THF (6 mL) was added n-BuLi (1.6 M in hexanes, 2.7 mL, 4.3 mmol) at −78° C. The reaction mixture was stirred for 0.5 h, followed by the addition of BF$_3$·Et$_2$O (0.54 mL, 4.3 mmol). Compound 33 (500 mg, 2.8 mmol) dissolved in dry THF (6 mL) was added to the reaction solution at −78° C. The reaction mixture was stirred for 2 h at −78° C. and then was quenched with saturated NH$_4$Cl (50 mL) and extracted with EtOAc (3×50 mL). The combined organic layer was washed with brine (50 mL), dried over MgSO$_4$, and concentrated under reduced pressure. The crude residue was purified by column chromatography on silica gel (hexane/EtOAc=10:1 to 6:1, v/v) to furnish compound 34 (418 mg, 57%) as colorless oil. $R_f$=0.42 (hexane/EtOAc=6:1, v/v).
$^1$H NMR (300 MHz, CDCl$_3$) δ7.48-7.21 (m, 5H), 4.55 (s, 2H), 3.94 (brs, 1H), 3.78-3.64 (m, 2H), 2.97 (d, J=3.3 Hz, 1H), 2.38 (brs, 2H), 2.18 (brs, 2H), 1.89-1.62 (m, 2H), 1.48-1.35 (m, 4H), 0.92 (t, J=6.9 Hz, 3H); $^{13}$C NMR (75 MHz, CDCl$_3$) δ138.1, 128.5, 127.8, 127.7, 82.9, 76.2, 73.4, 69.8, 68.7, 35.5, 31.2, 27.6, 22.0, 18.5, 13.7; MS (ESI) m/z calculated for C$_{17}$H$_{24}$O$_2$[M+N]$^+$, 283.2; found, 283.1.

Synthesis of Compound 35 ((R)-[1-(Benzyloxy)dec-5-yn-3-yl]oxy(tert-butyl)dimethylsilane)

To a solution of compound 34 (418 mg, 1.6 mmol) in CH$_2$Cl$_2$ (12 mL) were added imidazole (328 mg, 4.8 mmol) and TBDMSC$_1$ (363 mg, 2.4 mmol) slowly. The reaction mixture was stirred at 25° C. for 10 h and then was quenched with water (50 mL) and extracted with diethyl ether (3×50 mL). The combined organic layer was dried over MgSO$_4$, filtered, and concentrated under reduced pressure. The crude residue was purified by column chromatography on silica gel (hexane/EtOAc=15:1 to 7:1, v/v) to furnish compound 35 (538 mg, 87%) as colorless oil. $R_f$=0.95 (hexane/EtOAc=6:1, v/v).

$^1$H NMR (300 MHz, CDCl$_3$) δ7.48-7.21 (m, 5H), 4.52 (s, 3H), 3.96 (brs, 1H), 3.58 (t, J=6.3 Hz, 2H), 2.33 (brs, 1H), 2.16 (brs, 1H), 2.07-1.98 (m, 2H), 1.58-1.4 (m, 4H), 0.98-0.81 (m, 12H), 0.09 (s, 3H), 0.08 (s, 3H); $^{13}$C NMR (75 MHz, CDCl$_3$) δ138.7, 128.4, 127.7, 127.5, 82.1, 76.7, 72.9, 68.7, 67.0, 36.7, 31.2, 28.2, 25.9, 22.0, 18.6, 18.1, 13.7, 4.4, 4.7. MS (MALDI-TOF) m/z calculated for C$_{23}$H$_{38}$O$_2$Si [M+H]$^+$, 375.3; found, 375.4.

Synthesis of Compound 36 ((R)-3-[(tert-Butyldimethylsilyl)oxy]decan-1-ol)

To a solution of compound 35 (538 mg, 1.4 mmol) in MeOH (10 mL) was added 10% Pd/C (76 mg, 0.1 mmol). The reaction mixture was purged with H$_2$ and stirred for 3 h. The reaction mixture was filtered through a Celite pad and concentrated under reduced pressure. The crude residue was purified by column chromatography on silica gel (hexane/EtOAc=8:1, v/v) to furnish compound 36 (370 mg, 89%) as colorless oil. $R_f$=0.64 (hexane/EtOAc=6:1, v/v).
iH NMR (300 MHz, CDCl$_3$) δ3.93-3.83 (m, 2H), 3.76-3.70 (m, 1H), 2.50 (t, J=5.1 Hz, 1H), 1.98-1.78 (m, 1H), 1.75-1.61 (m, 1H), 1.61-1.48 (m, 2H), 1.41-1.21 (m, 10H), 0.98-0.82 (m, 12H), 0.11 (s, 3H), 0.10 (s, 3H); $^{13}$C NMR (75 MHz, CDCl$_3$) δ72.1, 60.4, 37.8, 37.0, 31.9, 29.8, 29.4, 26.0, 25.5, 22.7, 18.1, 14.2, 4.3, 4.6. MS (ESI) m/z calculated for C$_{16}$H$_{36}$O$_2$Si$^+$[M+H]$^+$, 289.2557; found, 289.2563.

Synthesis of Compound 37 ((R)-3-1(tert-Butyldimethylsilyl)oxyldecanoic acid)

Sodium periodate (1.6 g, 7.7 mmol) was added to a solution of compound 36 (370 mg, 1.3 mmol) in EtOAc (4 mL), acetonitrile (4 mL), and water (6 mL). The solution was stirred for 5 min Ruthenium trichloride (53 mg, 0.3 mmol) was added to the solution. The reaction mixture was stirred for 6 h and then was filtered through a Celite pad and washed with EtOAc (2×50 mL). The excess solvent was removed under reduced pressure, and the residue was partitioned between EtOAc (50 mL) and water (50 mL). The aqueous layer was extracted with EtOAc (3×50 mL). The combined organic layer was washed with brine (50 mL), dried over MgSO$_4$, and concentrated. The crude residue was purified by column chromatography on silica gel (hexane/EtOAc=8:1 to 4:1, v/v) to furnish compound 37 (260 mg, 67%) as colorless oil. $R_f$=0.38 (hexane/EtOAc=6:1, v/v).
$^1$H NMR (300 MHz, CDCl$_3$) δ4.11 (t, J=5.5 Hz, 1H), 2.53 (t, J=4.9 Hz, 2H), 1.55 (brs, 1H), 1.42-1.19 (brs, 10H), 0.99-0.81 (m, 12H), 0.12 (s, 3H), 0.10 (s, 3H); $^{13}$C NMR (75 MHz, CDCl$_3$) δ176.9, 69.6, 42.1, 37.4, 31.9, 29.7, 29.3, 25.88, 25.3, 22.8, 18.1, 14.2, 4.4, 4.7. MS (ESI) m/z calculated for C$_{16}$H$_{34}$O$_3$Si [M+H]$^+$, 303.2; found, 303.1.

Synthesis of Compound 38 ((R)-3-1(tert-Butyldimethylsilyl)oxyl-N-methoxy-N-methyldecanamide)

To a solution of compound 37 (260 mg, 0.9 mmol) in THF (10 mL) were added N,O-dimethylhydroxylamine hydrochloride (168 mg, 1.7 mmol), HOBt (158 mg, 1.0 mmol) and EDC hydrochloride (198 mg, 1.0 mmol). The solution was stirred for 5 min Diisopropylethylamine (0.45 mL, 2.6 mmol) was added. The reaction mixture was stirred at room temperature until the disappearance of the acid, as determined using TLC. The reaction mixture was concentrated, and the residue was partitioned between EtOAc (50 mL) and water (50 mL). The aqueous layer was extracted with EtOAc (3×25 mL). The combined organic layer was washed with brine (50 mL), dried MgSO$_4$, and concentrated. The crude residue was purified by column chromatography on silica gel (hexane/EtOAc=10:1 to 6:1, v/v) to furnish compound 38 (276 mg, 93%) as colorless oil. R$_f$=0.44 (hexane/EtOAc=6:1, v/v).

$^1$H NMR (300 MHz, CDCl$_3$) δ4.21 (t, J=5.5 Hz, 1H), 3.69 (s, 3H), 3.18 (s, 3H), 2.81-2.62 (m, 2H), 2.39 (dd, J=4.5 and 14.6 Hz, 1H), 1.54-1.41 (m, 2H), 1.44-1.13 (m 10H), 0.94-0.83 (m, 12H), 0.07 (s, 3H), 0.03 (s, 3H); $^{13}$C NMR (75 MHz, CDCl$_3$) δ172.7, 69.6, 61.4, 39.7, 38.0, 31.9, 29.8, 29.4, 26.0, 25.2, 22.7, 18.1, 14.2, 4.6, 4.6. MS (MALDI-TOF) m/z calculated for C$_{18}$H$_{39}$NO3Si [M+H]$^+$, 346.3; found, 346.2.

Synthesis of Compound 39 ((R)-4-1(tert-Butyldimethylsilyl)oxylundecan-2-one)

To a solution of compound 38 in THF (10 mL) was added methylmagnesium bromide (3 M solution in ether, 0.8 mL, 2.4 mmol) at −78° C. The reaction mixture was stirred for 2 h at the same temperature and then was poured into saturated aqueous NH$_4$Cl (25 mL) and diluted with EtOAc. The aqueous layer was extracted with EtOAc (3×25 mL). The combined organic layer was washed with brine (25 mL), dried MgSO$_4$, and concentrated under reduced pressure. The crude residue was purified by column chromatography on silica gel (hexane/EtOAc=10:1, v/v) to furnish compound 39 (216 mg, 90%) as colorless oil. R$_f$=0.53 (hexane/EtOAc=8:1, v/v).

$^1$H NMR (300 MHz, CDCl$_3$) δ4.13 (t, J=5.5 Hz, 1H), 2.60 (dd, J=6.9 and 15.0 Hz, 1H), 2.46 (dd, J=4.8 and 14.9 Hz, 1H), 2.16 (s, 3H), 1.49-1.38 (m, 2H), 1.49-1.18 (m, 10H), 0.98-0.82 (m, 12H), 0.06 (s, 3H), 0.02 (s, 3H); $^{13}$C NMR (75 MHz, CDCl$_3$) 208.1, 69.3, 51.0, 37.8, 31.9, 31.8, 25.9, 24.8, 22.7, 18.1, 14.1, 4.5, 4.7. MS (MALDI-TOF) m/z calculated for C$_{17}$H$_{36}$O$_2$Si [M+Na]$^+$, 323.2; found, 323.2.

Synthesis of Compound 40 ((R)-6-Heptyl-2,2,8,8,9,9-hexamethyl-4-methylene-3,7-dioxa-2,8-disiladecane)

To a solution of compound 39 (200 mg, 0.7 mmol) in CH$_2$Cl$_2$ (10 mL) were added diisopropylethylamine (258 mg, 2.0 mmol) and TMSOTf (0.27 mL, 1.0 mmol) at 0° C. The reaction mixture was stirred for 3 h at 0° C. and then was quenched with saturated aqueous NaHCO$_3$ (20 mL) and extracted with CH$_2$Cl$_2$. The organic layer was washed with water and brine, dried over MgSO$_4$, filtered, and concentrated under reduced pressure. The crude residue dissolved in diethyl ether (20 mL) was washed with water and brine, dried over MgSO$_4$, filtered, and concentrated under reduced pressure to provide compound 40 which was used in the next step without further purification. R$_f$=0.89 (hexane/EtOAc=8:1, v/v).

Synthesis of Compound 41 ((R,E)-5-Hydroxy-1-(4-hydroxy-3-methoxyphenyl)dodec-1-en-3-one, Formula 27)

To a mixture of compound 40 and vanillin (108 mg, 0.7 mmol) in CH$_2$Cl$_{12}$ (10 mL) was added BF$_3$.OEt$_2$ (0.312 mL, 1.2 mmol) over 10 min at 0° C. The reaction mixture was stirred for 30 min at 0° C. Triethylamine (0.494 mL, 6.0 mmol) was added in one portion to the reaction mixture. The reaction mixture was stirred for 20 min and then was quenched with saturated aqueous NaHCO$_3$ (10 mL) and extracted with CH$_2$Cl$_2$. The organic layer was washed with water and brine, dried over MgSO$_4$, filtered, and concentrated under reduced pressure. The crude residue was purified by column chromatography on silica gel (hexane/EtOAc=5:1 to 2:1, v/v) to furnish compound 41 (41 mg, 18% over 2 steps). R$_f$=0.32 (hexane/EtOAc=4:1, v/v).

$^1$H NMR (300 MHz, CDCl$_3$) δ7.53 (d, J=16.1 Hz, 1H), 7.10 (d, J=8.1 Hz, 1H), 7.06 (s, 1H), 6.94 (d, J=8.1 Hz, 1H), 6.61 (d, J=16.2 Hz, 1H), 5.93 (s, 1H), 4.15 (brs, 1H), 3.96 (s, 3H), 3.31 (s, 1H), 2.90 (d, J=16.5 Hz, 1H), 2.75 (dd, J=9.3 and 17.3 Hz, 1H), 1.63-1.21 (m, 12H), 0.98-0.82 (m, 3H); $^{13}$C NMR (75 MHz, CDCl$_3$) δ201.0, 148.6, 146.9, 143.8, 126.7, 124.2, 123.7, 114.9, 109.5, 68.0, 56.0, 46.5, 36.6, 31.8, 29.6, 29.3, 25.6, 22.7, 14.1. MS (MALDI-TOF) m/z calculated for C$_{19}$H$_{28}$O$_4$+[M+H]$^+$,321.2; found, 321.4.>99% purity (as determined by RP-HPLC, method B, t$_R$=9.51 min).

Synthesis of Compound 42 ((R)-5-Hydroxy-1-(4-hydroxy-3-methoxyphenyl)dodecan-3-one, Formula 28)

To compound 41 (20 mg, 0.06 mmol) dissolved in MeOH (5 mL) was added 10% Pd/C (1.2 mg, 0.01 mmol). The reaction mixture was purged with H$_2$ gas and stirred for 1 h. The reaction mixture was filtered through a Celite pad and then was concentrated under reduced pressure. The crude residue was purified by column chromatography on silica gel (hexane/EtOAc=3:1, v/v) to furnish compound 42 (19 mg, 95%) as colorless oil. R$_f$=0.29 (hexane/EtOAc=4:1, v/v).

$^1$H NMR (300 MHz, CDCl$_3$) δ6.84 (d, J=7.9 Hz, 1H), 6.69 (s, 1H), 6.68 (d, J=7.9 Hz, 1H), 5.50 (s, 1H), 4.04 (brs, 1H), 3.89 (s, 3H), 2.95 (brs, 1H), 2.93-2.81 (m, 2H), 2.81-2.72 (m, 2H), 2.61-2.45 (m, 2H), 1.51-1.22 (m, 12H), 0.88 (d, J=6.7 Hz, 3H); $^{13}$C NMR (75 MHz, CDCl$_3$) δ211.6, 146.6, 144.1, 132.8, 120.9, 114.5, 111.1, 67.8, 56.0, 49.5, 45.6, 36.6, 31.9, 29.6, 29.4, 29.4, 25.6, 22.8, 14.2. MS (MALDI-TOF) m/z calculated for C$_{19}$H$_{30}$O$_4^+$[M]$^+$, 322.2; found, 322.2.>99% purity (as determined by RP-HPLC, method B, t$_R$=9.53 min).

Kinetic Resolution by Chiral HPLC

The ee values of 8-gingerol were determined by chiral HPLC analyses on a chiral column (CHIRALPAK IG; 4.6 mm i.d.×250 mm). Chromatographic analyses were carried out on an HPLC system (Agilent 1260 series) for 30 min at a flow rate of 1 mL/min with an isocratic solution of 20% ethanol in hexane. The autosampler and the column compartment temperatures were set to 25° C. UV detection was conducted at a wavelength of 230 nm; 5 μL of the sample was injected with three repeats at each concentration.

LasR Reporter Gene Assay

This assay was conducted by modifying a previously reported method. *E. coli* DH5α co-transformed with two plasmids, pJN105L (LasR expression plasmid) and pSC$_{11}$ (lasI::lacZ fusion plasmid), was used as a bioassay reporter strain. Overnight culture of the reporter strain with 10 μg/mL gentamicin and 50 μg/mL ampicillin was diluted in the Luria-Bertani (LB) medium (1:100). Then, the reporter strain (optical density at 595 nm [OD595] was 0.3) mixed with either a positive control or the synthesized compound was incubated with OdDHL (Sigma-Aldrich, St. Louis, MO., USA) and 0.4% arabinose (Sigma-Aldrich). After incubation at 37° C. for 1.5 h, OD$_{595}$ was measured on a VICTOR ×5 multimode plate reader (PerkinElmer, Waltham, Mass., USA). The β-galactosidase activity was determined using a Tropix plus kit (Applied Biosystems, USA), and luminescence was measured on the VICTOR ×5 multimode plate reader. RLU ratio was quantified by dividing luminescence with $OD_{595}$.

Static Biofilm Formation Assay

Overnight culture of *P. aeruginosa* PA14 ($OD_{595}$=1.0) was diluted (1:20) with the AB medium (300 mM NaCl, 50 mM $MgSO_4$, 0.2% vitamin-free casamino acids, 10 mM potassium phosphate, 1 mM L-arginine, and 1% glucose, pH 7.5) (1:20) containing with either positive controls or synthesized compounds (0-100 μM). The dilutions were aliquoted into borosilicate bottles, and the bottles were incubated at 37° C. for 24 h without agitation. After that, $OD_{595}$ of the cell suspension was measured on the VICTOR ×5 multimode plate reader. The biofilm cells attached to the bottle were washed two times with phosphate buffered saline (PBS; 137 mM NaCl, 2.7 mM KCl, 10 mM $Na_2HPO_4$, and 2 mM $KH_2PO_4$, pH 7.2) and stained with 0.1% crystal violet for 10 mM Next, the stained biofilm cells were eluted with 100% ethyl alcohol, and $OD_{540}$ was measured on the VICTOR ×5 multimode plate reader. The biofilm formation was quantified by dividing $OD_{540}$ with $OD_{595}$.

Dynamic Biofilm Formation Assay

Glass slides were dipped into a Petri dish containing 2 mL of a *P. aeruginosa* PA14 suspension ($OD_{595}$=1.0) and 18 mL of the AB medium, followed by incubation at 37° C. for 24 h to let the cells adhere to the slides. The slides were then inserted into a drip-flow reactor (DFR-110, BioSurface, Mont., USA). The AB medium with either a positive control or the synthesized compound (0-10 μM) was fed into the reactor continuously via a peristaltic pump (Masterflex C/L tubing pumps, Cole-Parmer, IL, USA) at 0.3 mL/min After operation of the reactor at 37° C. for 48 h, the cells on the slides were washed two times with PBS. The biofilm cells were stained with fluorescein isothiocyanate-labeled type IV ConA (Sigma-Aldrich) and SYPRO Ruby (Ruby, Invitrogen, Carlsbad, CA, USA) for 15 min, respectively. CLSM images were captured via a 20× objective lens (W N-Achroplan 20×/0.5 W [DIC] M27) with green fluorescence (ConA, excitation wavelength of 490 nm, emission wavelength of 525 nm) and red fluorescence (Ruby, excitation wavelength of 470 nm, emission wavelength of 618 nm) and were analyzed in the Zen 2011 software (Carl Zeiss, Jena, Germany). For quantification, biofilm volume ($\mu m^3/\mu m^2$) and average thickness (μm) were measured by means of Comstat2 in ImageJ.

Growth Inhibition Assay

A 5% dilution of overnight culture of *P. aeruginosa* PA14 ($OD_{595}$=1.0) containing either a positive control or the synthesized compound (0-100 μM) was inoculated into wells of a 96-well polystyrene microtiter plate (Sigma-Aldrich). The plate was incubated at 37° C. for 24 h. $OD_{595}$ of the suspension culture was measured on the VICTOR ×5 multimode plate reader.

In Silico Docking Study of Compounds 41 and 42 with LasR

The processes of ligand preparation and optimization were conducted by means of the Prepare Ligands module, a protocol of Discovery Studio 3.0 (Accelrys Inc.). The prepared ligands were converted to the SD file format. LasR Protein structure in PDB format was downloaded from the RCSB Web site (http://www.pdb.org). Before the docking procedure, the original crystal ligand OdDHL and water molecules were removed from the protein-ligand complexes. Hydrogen atoms were added by application of CHARMm force field and the Momany-Rone partial charge as default settings in Discovery Studio 3.0. The ligand-binding site was extracted from PDB site records and designated as active site 1. Docking analyses of compound 41 or 42 with the LasR protein in the presence of OdDHL were performed by means of the CDOCKER module. The number of generated poses was set to 100 for each ligand, and default settings were selected for other parameters.

Statistical Analysis

P values were estimated by Student's t test (SigmaPlot version 10, Systat Software Inc., San Jose, Calif., USA).

RESULTS AND DISCUSSION

Structural modification of (S)-6-gingerol was attempted based on key interactions between (S)-6-gingerol and LasR of *P. aeruginosa*. Chemical structure of (S)-6-gingerol was subdivided into three parts (head, middle, and tail sections) as shown in FIG. 2. The effect of each section on LasR-binding affinity and on biofilm formation was investigated.

In the head section, the methoxy group at the 3'-position and/or the hydroxyl group at 4'-position of the phenyl moiety was replaced with other functional groups to determine whether the hydrogen-bonding interaction is necessary or not. Regarding the modification of the middle section, a double bond was introduced between the phenyl moiety and the carbonyl group to assess the influence of rotational flexibility. The necessity of the hydroxyl group and the effect of stereochemistry of the chiral center on the affinity for LasR and on biofilm formation were also evaluated. In the tail section, an experiment was conducted to find the optimal alkyl chain length for a maximized van der Waals interaction with the LasR hydrophobic subpocket, which is formed by lipophilic amino acid residues (Leu36, Leu40, Ala50, Ile52, Ala70, Val76, and Leu125).

First, gingerol analogs with various alkyl chain length from 4-gingerol to 10-gingerol were synthesized to find the optimal carbon length in the tail section. As shown in Scheme 1, compound 2 was synthesized from commercial vanillin by treatment with 10% NaOH in acetone at 25° C. for 16 h in 71% yield. Compound 3 was obtained by reacting compound 2 with hydrogen gas in methanol in the presence of 10% Pd/C at 25° C. for 2 h in 97% yield. Treatment of compound 3 with lithium diisopropylamide (LDA) at −78° C., followed by the addition of appropriate aldehydes (butanal for compound 4, pentanal for compound 5, hexanal for compound 6, heptanal for compound 7, octanal for compound 8, nonanal for compound 9, and decanal for compound 10), afforded the final gingerol compounds in 30-47% yield.

LasR-binding affinity of the synthesized gingerols (compounds 4-10) with various alkyl chain lengths was determined by measuring luminescence of an *E. coli* reporter strain. The reporter strain carried two plasmids, pJN105L (LasR expression plasmid) (Lee, J. H.; Lequette, Y.; Greenberg, E. P. Activity of purified QscR, a *Pseudomonas aeruginosa* orphan quorum-sensing transcription factor. Mol. Microbiol. 2006, 59, 602609.) and pSC11 (las1::lacZ fusion plasmid) (Chugani, S. A.; Whiteley, M.; Lee, K. M.; D'Argenio, D.; Manoil, C.; Greenberg, E. P. QscR, a modulator of quorum-sensing signal synthesis and virulence in *Pseudomonas aeruginosa*. Proc. Natl. Acad. Sci. U.S.A. 2001, 98, 27522757.), which enabled assay of competitive binding of OdDHL with each gingerol derivative 4-10. Antagonistic activities of the synthesized compounds at 1 μM or 10 μM were determined by measuring luminescence in the presence of 1 μM OdDHL (compound 1a) and presented as relative luminescence unit (RLU) ratio. Three compounds (compounds 1b, 1c, and 1d) served as positive controls. As shown in FIG. 3, LasR-antagonistic activities increased as the alkyl chain lengthened, indicating that the longer alkyl group contributed to the affinity for LasR via the van der Waals interaction in the hydrophobic subpocket of LasR. Just as the LasR inhibition, inhibition of biofilm formation also strengthened as the carbon chain was extended at 10 μM ((B) of FIG. 3). However, inhibition of biofilm formation decreased with 9-gingerol (compound 9) and 10-gingerol (compound 10) at 100 μM ((C) of FIG. 3) because of increased bacterial growth inhibition. As shown in (D) of FIG. 3, compounds 9 and 10 with a longer alkyl chain inhibited bacterial growth significantly at 100 μM as compared with the other compounds. This effect may be due to the fact that compounds 9 and 10 act as a surfactant, which inhibits bacterial growth. Agonistic activities of compounds 4-10 in an *E. coli* reporter assay system in the absence of OdDHL were next examined. None of them showed agonistic activity to LasR at 10 μM (not shown).

On the basis of results of LasR antagonism and biofilm formation of compounds 4-10, 6- and 8-gingerol derivatives with various functional groups in the head section were prepared. 6-Gingerol derivatives (compounds 14a-20a) were prepared from commercial vanillin in three steps. Briefly, treatment of various benzaldehydes with acetone afforded analogs of compound 12 in 35-75% yield. Catalytic hydrogenation of the unsaturated alkene group produced analogs of compound 13 in 75% yield. 6-Gingerol analogs (compounds 14a-20a) with various substituents in the head section were obtained by reacting compound 13 with n-hexanal as shown in Scheme 2, whereas 8-gingerol derivatives (compounds 14b-20b) were done with n-octanal instead of n-hexanal.

LasR-antagonistic activities of 6- and 8-gingerol derivatives modified in the head section were evaluated. Hydrogen-bonding effects of the methoxy group at the 3'-position and the hydroxyl group at the 4'-position of the phenyl moiety in 6-gingerol analogs were evaluated by introducing other functional groups. As shown in (A) of FIG. 4, removal of the methoxy and hydroxyl group together (compound 15a) significantly decreased the LasR-antagonistic activity, implying that at least one hydrogen-bonding interaction is required for binding to LasR. When only the methoxy group at the 3'-position was removed (compound 18a), this change increased the LasR-antagonistic activity. In contrast, removal of the hydroxyl group at the 4'-position (compound 20a) decreased the LasR-antagonistic activity. These results suggested that substituents capable of hydrogen bonding at the 4'-position were more favorable for binding to LasR. Replacement of OH at the 4'-position with F preserved the LasR-inhibitory activity (compound 16a vs compound 1b and compound 17a vs compound 18a), suggesting that the functional group at 4'-position may act as a hydrogen-bonding acceptor rather than a hydrogen-bonding donor.

LasR inhibition patterns of 8-gingerol derivatives were similar to those of 6-gingerol. As shown in (C) of FIG. 4, compounds 17b and 18b with a substitution by a hydrogen-bond acceptor at the 4'-position were the most potent among the synthesized compounds. Activities of compounds 15b and 20b without any hydrogen-bonding acceptor at the 4'-position were relatively weaker than those of the other compounds. In general, LasR inhibition by 8-gingerol derivatives was stronger than the corresponding 6-gingerol ones. The static biofilm formation assay of 6- and 8-gingerol derivatives with variation in the head section showed a tendency similar to that in the LasR inhibition assay ((B) of FIG. 4 and (D) of FIG. 4). Compounds with a hydrogen-bonding acceptor at the 4'-position (compounds 16a, 16b, 17a, 17b, 18a, and 18b) were the most potent in the series. This result was consistent with the hypothesis that derivatives with stronger affinity for LasR can inhibit biofilm formation more effectively. Compounds 16b, 17b, and 18b exerted stronger inhibition of biofilm formation than the known anti-biofilm agent (S)-6-gingerol (compound 1b).

To assess the effect of rotational flexibility between the head section and the carbonyl group, several compounds 21a, 21b, 22a, and 22b were prepared in 30-35% yield via crossed aldol condensation (Scheme 3). In addition, compounds 24a and 24b were prepared to determine the necessity of the β-hydroxy group for the LasR-binding affinity and for the inhibition of biofilm formation. Reaction of vanillin with 2-nonanone or 2-dodecanone in the presence of L-proline gave compounds 23a and 23b in 45% and 60% yield, respectively. Compounds 24a and 24b were prepared in 80% and 97% yield by subjecting compounds 23a and 23b to hydrogenation conditions ($H_2$, Pd/C) for 2 h.

As shown in FIG. 5, compounds 21a and 21b (restricted rotation) showed slightly stronger LasR affinity than did the corresponding compounds 6 and 8 with flexible rotation. The derivatives (compounds 23a, 23b, 24a, and 24b) without the β-hydroxyl group showed significantly weaker LasR-binding affinity and less inhibition of biofilm formation than the ones with the β-OH group. These data suggested that the OH group at the β-position of the carbonyl group may play a pivotal role in the binding to the LasR protein as well as in the inhibition of *P. aeruginosa* biofilm formation.

Results on in vitro LasR-binding and inhibition of biofilm formation indicated that 8-gingerol analogs were more potent than 6-gingerol analogs. Furthermore, a racemic mixture of 6-and 8-gingerol (compounds 6 and 8) was slightly more potent than the pure (S)-enantiomer of 6-gingerol (compound 1b) or 8-gingerol (compound 1c). Therefore, it was hypothesized that the pure (R)-enantiomer of gingerol would possess stronger LasR-binding affinity and inhibition of biofilm formation than the corresponding (S)-enantiomer. Enantiomerically enriched (R)- and (S)-enantiomers of 8-gingerol were synthesized by means of chiral catalysts such as D-proline and Salen' s catalyst.

Scheme 4 shows the synthetic approach to enantiomerically enriched (R)-8-gingerol (compound 29) using D-proline as a chiral catalyst. Compound 25 was synthesized from 1-octanal by treatment with D-proline in acetone at room temperature for 48 h. Acetone served as a reagent and solvent in the reaction. Compound 25 was obtained by treatment with imidazole and tert-butyldimethylsilyl chloride ($TBDMSC_1$) in dichloromethane to give compound 26 (87% yield). Silyl enol ether compound 27 was obtained by treating compound 26 with trimethylsilyl trifluoromethanesulfonate (TMSOTf) and N,N-diisopropylethylamine (DIPEA). The Mukaiyama aldol reaction between compound 27 and vanillin, with simultaneous removal of the TBDMS group using boron trifluoride ($BF_3$), afforded compound 28 (65% yield) in two steps. Catalytic hydrogenation of compound 28 produced the final compound 29 in 97% yield. The % enantiomeric excess (ee) value of compound 29 was determined by chiral HPLC analysis.

The synthetic strategy for enantiomerically enriched (R)-8-gingerol (compound 42) using Salen' s catalyst is described in Scheme 5. Briefly, compound 31 was synthesized from commercial 3-buten-1-ol via treatment with sodium hydride and benzyl bromide in THF at 0° C. for 16 h. Reaction of compound 31 with m-CPBA and $NaHCO_3$ in $CH_2Cl_2$ at 0° C. for 16 h gave a racemic mixture of epoxide compound 32 in 72% yield.

The (S)-epoxide compound 33 was obtained by reacting compound 32 with (S,S)-(+)-N,N'-bis(3,5-di-tert-butylsalicyclidene)-1,2-cyclohexanediaminocobalt(II) (Salen' s catalyst). Lithiation of the terminal alkyne of 1-hexyne with n-BuLi, followed by the addition of compound 33, afforded compound 34 in 57% yield via an epoxide ring-opening reaction. The hydroxyl group of compound 34 was protected with TBDMSCl to obtain compound 35. Debenzylation of compound 35 by means of $H_2$ and Pd/C provided primary alcohol compound 36 in 89% yield. Treatment of compound 36 with $NaIO_4$ and $RuCl_3$ oxidized the primary alcohol to the carboxylic acid, thus producing compound 37 in 67% yield. The carboxylic acid was transformed into Weinreb amide compound 38 by using N,O-dimethylhydroxylamine under peptide-coupling conditions (HOBt and EDC). Reaction of compound 38 with methylmagnesium bromide in THF afforded compound 39 in 90% yield. Compound 40 was generated by reacting compound 39 with TMSOTf and DIPEA in dichloromethane. The Mukaiyama aldol reaction between compound 40 and vanillin, with simultaneous deprotection of the TBDMS group using $BF_3$, afforded compound 41 (65% yield) in two steps. The final compound 42 was obtained in 97% yield by reducing the double bond of α,β-unsaturated ketone compound 41 under catalytic hydrogenation conditions. The (S)-isomer of 8-gingerol (compound 42S) was prepared in a similar way, where (R,R)-(+)-N,N'-bis(3,5-di-tert-butylsalicyclidene)-1,2-cyclohexanediaminocobalt(II) was used.

As shown FIG. 6, Scheme 1 without a chiral catalyst produced a racemic mixture of 8-gingerol (compound 8) at an almost 1:1 ratio in a chiral HPLC experiment ((A) of FIG. 6). Scheme 4, in which D-proline served as a chiral catalyst, generated compound 29 with a 70% ee value ((B) of FIG. 6). As expected, Scheme 5 by means of Salen' s catalyst afforded (S)-8-gingerol (compound 42S) and (R)-8-gingerol (compound 42) with ee value of >95% ((C) and (D) of FIG. 6).

LasR-binding affinity of the synthesized (R)- and (S)-8-gingerol compounds was evaluated in a luminescent reporter assay. The activity of (S)-8-gingerol (compound 42S) synthesized using Salen's catalyst was almost the same as that of commercial (S)-8-gingerol (compound 1c). As the proportion of the (R)-enantiomer of 8-gingerol increased, LasR-binding affinity was strengthened accordingly. The enantiomerically enriched (R)-8-gingerol compound 42 showed much stronger LasR-binding affinity than compound 1c, as was the case for a racemic mixture of 8-gingerol (compound 8). Compound 29 with an ee value of 70% had the intermediate LasR-affinity between compound 8 and compound 42 ((A) of FIG. 7). As shown in (B) of FIG. 7, the results of the static biofilm formation assay indicated a trend similar to that of the affinity for LasR. Compound 42 yielded 72% biofilm formation when the effect of compound 1c was set to 100%. Effects of absolute configuration on the interaction between QS chemical signals and their cognate receptors have been investigated. The (R)-enantiomer of 8-gingerol (compound 42) manifested stronger LasR-binding affinity than the synthesized (S)-enantiomer (compound 42S) and the commercial compound 1c.

Because compound 21b (a racemic mixture) with restricted rotation between the carbonyl group and phenyl moiety was more potent than compound 1c (FIG. 5), compound 41 was assumed to be more potent than compound 42. As expected, compound 41 showed stronger LasR-binding affinity and greater inhibition of biofilm formation than compound 42 (FIG. 7). However, bacterial growth inhibition was not observed even at 100 μM concentration of compounds 41 and 42 (not shown). In order to evaluate the binding reversibility of compound 41 to LasR, LasR binding activities of compound 41 (1 μM) were measured for different concentrations of compound 1a (0, 0.1, 1, 10, and 100 μM). By increasing concentration of compound 1a, the differences in LasR binding activities between the group treated with compound 41 and the control (no treatment of compound 41) decreased (not shown). At 100 μM compound 1a, LasR-agonistic activity in the treatment group was completely recovered and almost the same as the control one. This result suggests that compound 41 binds reversibly to LasR by competing with compound 1a.

A dynamic biofilm formation assay of compounds 41 and 42 was performed in a drip-flow reactor. Compound 1c served as a positive control, and DMSO served as a negative control. After 48 h drip-flow reactor operation, the biofilm was stained with Ruby and concanavalin A (ConA). Ruby (red) is a reagent for staining protein, and ConA (green) is for carbohydrate of biofilm. As shown in (A) of FIG. 8, the biofilm in the presence of DMSO formed with typical mushroom-like morphology. By contrast, the biofilms treated with compound 1c ((B) of FIG. 8), compound 42 ((C) of FIG. 8), or compound 41 ((D) of FIG. 8) were relatively thin and sparse as compared with the negative control. Biofilm volume and thickness with compound 41 were the lowest among the three groups (Table 1).

TABLE 1

| Characteristic | DMSO | 1c | 41 | 42 |
| --- | --- | --- | --- | --- |
| Biofilm volume ($\mu m^3/\mu m^2$) | 23.1 ± 1.8 | 17.0 ± 0.4 | 7.4 ± 0.2 | 9.7 ± 1.1 |
| Biofilm thickness (μm) | 34.5 ± 1.3 | 17.0 ± 0.4 | 10.3 ± 0.1 | 13.9 ± 0.1 |

Furthermore, the biofilm treated with compound 41 showed a relatively smaller volume of carbohydrates (47-74%) and proteins (23-56%) as compared to the other groups. Comprehensive analysis of confocal laser scanning microscopy (CLSM) images of biofilms indicated that the (R)-8-gingerol analogs (compound 41 and compound 42) inhibited biofilm formation more effectively than compound 1c did. To explain why compounds 41 and 42 showed strong LasR-binding affinity and potent inhibition of biofilm formation, molecular docking analyses of compounds 41 and 42 and their (S)-enantiomers (compounds 41S and 42S) were conducted by using the crystal structure of LasR (PDB code 2UV0). The ligands were docked to the LasR active site by means of the CDOCKER module of Discovery Studio (Accelrys Inc., San Diego, CA, USA). The best-docked pose of each ligand in the active site coincided well with the crystal ligand OdDHL. Moreover, compound 41 engaged in a much greater number of hydrogen-bonding interactions with LasR than the other three ligands did. As shown in (A) of FIG. 9, compound 41 participated in hydrogen-bonding interactions with Tyr47, Arg61, Asp65, Asp73, and Tyr93. In particular, the OH group at the 4'-position of the phenyl moiety was deeply projected toward Tyr93 and formed polar interactions, which were not observed in the other ligands. Furthermore, it was noteworthy that the β-hydroxyl group of compound 41 participated in strong hydrogen-bonding interactions with the guanidinium group of Arg61. In addition, the lipophilic alkyl group made hydrophobic contacts with lipophilic amino acid residues including Leu39, Leu40, and Leu125. Tight packing between the surrounding amino acid residues and compound 41 contributed substantially to the stability of the protein-ligand complex; this phenomenon may explain the strong potency of compound 41. In contrast, compounds 42

((B) of FIG. 9), compound 41S, and compound 42S had a relatively small number of hydrogen-bonding interactions with LasR.

INDUSTRIAL APPLICABILITY

On the basis of the chemical structure of (S)-6-gingerol, which is a potent anti-biofilm agent, a variety of 6- and 8-gingerol analogs were synthesized. These compounds were designed to evaluate the effects of the head, middle, and tail sections of 6-gingerol on LasR-binding affinity and on biofilm formation. Regarding modification of the tail section, affinity for LasR and inhibition of biofilm formation increased as the alkyl chain lengthened up to 8-gingerol. As for modification of the head section, compounds with a substitution by a hydrogen-bonding acceptor group (e.g., F or OH) at the 4'-position were the most potent, indicating that the hydrogen-bonding interaction was essential for binding to LasR. In the variants of the middle section, β-OH of the carbonyl group was necessary, whereas rotational rigidity between the head section and carbonyl group was favorable for LasR-binding affinity and for inhibition of biofilm formation. To evaluate the effects of stereochemistry, enantiomerically enriched (R)-8-gingerol was synthesized by means of chiral catalysts such as D-proline and Salen's catalyst. The results suggested that the stereochemistry of 8-gingerol is one of the important factors for the enhancement of LasR-binding affinity and inhibition of biofilm formation.

In conclusion, the synthesized gingerol derivatives were found to have strong binding affinity for LasR and inhibition of biofilm formation. Therefore, the gingerol derivatives can act on various membrane surfaces where biofilms tend to form and can effectively inhibit the formation of the corresponding biofilms. In addition, the use of the pharmaceutical composition according to the present invention is expected to fundamentally prevent or treat a variety of infections caused by biofilms due to the presence of the gingerol derivative in the pharmaceutical composition.

The invention claimed is:

1. A gingerol derivative represented by Formula 13 to 17, 20 to 22, 25, and 26:

[Formula 13]

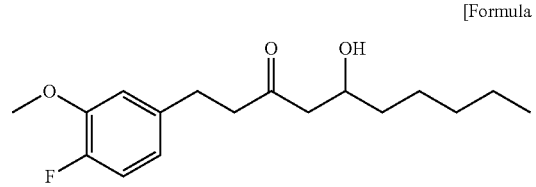

[Formula 14]

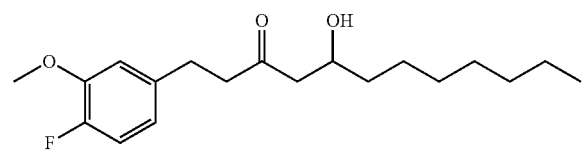

[Formula 15]

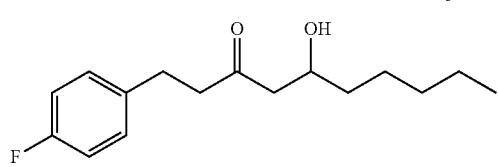

[Formula 16]

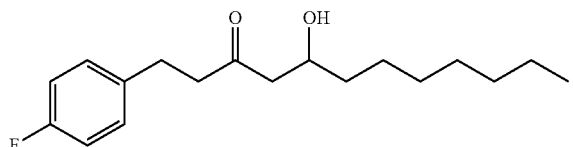

[Formula 17]

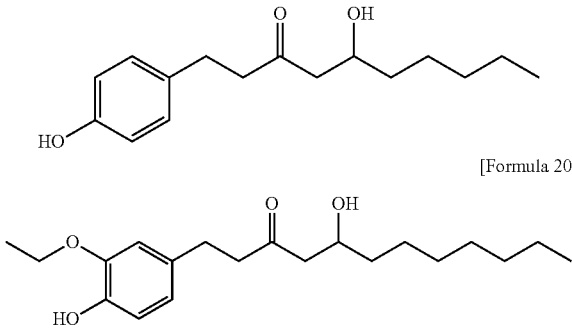

[Formula 20]

[Formula 21]

[Formula 22]

[Formula 25]

[Formula 26]

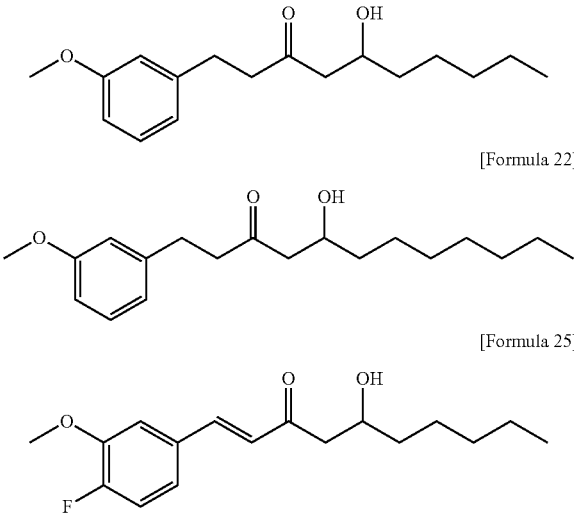

2. The gingerol derivative according to claim 1, wherein the gingerol derivative inhibits biofilm formation.

3. The gingerol derivative according to claim 2, wherein the biofilm is formed by one or more bacterial species selected from the group consisting of *Pseudomonas aeruginosa, Salmonella* spp., *Shigella* spp., *Vibrio parahaemolyticus, Vibrio choreae, Escherichia coli* O-157, *Campylobacter jejuni, Clostridium difficile, Clostridium perfringens, Yersinia enterocolitica, Helicobacter pylori, Entemoeba histolytica, Bacillusu cereus, Clostridium botulinum, Haemophilus influenzae, Streptococcus pneumoniae, Chlamidia pneumoniae, Legionella pneumoniae, Branhamella catarrhalis, Mycobacterium tuberculosis, Mycoplasma pneumoniae, Storeptcoccus pyogenes, Corynebacterium diphtheriae, Bordetella pertussis, Chramidia psittaci*, methicillin resistant *Staphylococcus aureus* (MRSA), *Escherichia coli*,

*Klebsiella pneumoniae, Enterobacter* spp., *Proteus* spp., *Acinetobacter* spp., *Enterococcus faecalis, Staphylococcus saprophyticus*, and *Storeptcoccus agalactiae*.

4. A composition for inhibiting biofilm formation comprising the gingerol derivative according to claim 1.

5. A pharmaceutical composition for preventing or treating infections caused by biofilms comprising the gingerol derivative according to claim 1 or a pharmaceutically acceptable salt thereof as an active ingredient.

6. The pharmaceutical composition according to claim 5, wherein the infections are selected from the group consisting of cystic fibrosis, pneumonia, dental caries, periodontitis, otitis media, musculoskeletal infections, necrotizing fasciitis, biliary tract infection, osteomyelitis, bacterial prostatitis, native valve endocarditis, melioidosis, nosocomial infection, ICU pneumonia, urinary catheter cystitis, peritoneal dialysis (CAPD) peritonitis, and biliary stent blockage.

\* \* \* \* \*